US009436158B2

(12) United States Patent
Kostuk et al.

(10) Patent No.: US 9,436,158 B2
(45) Date of Patent: Sep. 6, 2016

(54) VOLUME HOLOGRAPHIC IMAGING SYSTEM (VHIS) ENDOSCOPE

(71) Applicant: The Arizona Board of Regents on Behalf of the University of Arizona, Tucson, AZ (US)

(72) Inventors: Raymond K. Kostuk, Tucson, AZ (US); Paul J. Gelsinger-Austin, Pine Hill, NJ (US); Johnathan W. Brownlee, Tucson, AZ (US); Jennifer K. Barton, Tucson, AZ (US); Erich de Leon, Lake Shore, MD (US); Michael Gordon, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 347 days.

(21) Appl. No.: 14/353,148

(22) PCT Filed: Oct. 19, 2012

(86) PCT No.: PCT/US2012/061196
§ 371 (c)(1),
(2) Date: Apr. 21, 2014

(87) PCT Pub. No.: WO2013/059727
PCT Pub. Date: Apr. 25, 2013

(65) Prior Publication Data
US 2015/0103140 A1    Apr. 16, 2015

Related U.S. Application Data

(60) Provisional application No. 61/628,000, filed on Oct. 21, 2011, provisional application No. 61/633,925, filed on Feb. 21, 2012.

(51) Int. Cl.
*H04N 5/89*      (2006.01)
*G03H 1/10*      (2006.01)
(Continued)

(52) U.S. Cl.
CPC ......... *G03H 1/0005* (2013.01); *A61B 1/00163* (2013.01); *G02B 23/243* (2013.01);
(Continued)

(58) Field of Classification Search
CPC .. H04N 7/183; G03H 1/0005; G03H 1/0248; G03H 1/0443; A61B 1/00163
See application file for complete search history.

(56) References Cited

U.S. PATENT DOCUMENTS 5,743,846 A  *  4/1998  Takahashi .......... G02B 23/2415
                                                    600/111
6,801,347 B2     10/2004  Nakamura
(Continued)

FOREIGN PATENT DOCUMENTS

WO    2011/044460 A1    4/2011
WO    2012/040639 A2    3/2012

OTHER PUBLICATIONS

Aiello, L., et al., "Green's Formulation for Robust Phase Unwrapping in Digital Holography," Optics and Lasers in Engineering 45(6):750-755, Jun. 2007.
Castro, J.M., et al., "Analysis of Diffracted Image Patterns From Volume Holographic Imaging Systems and Applications to Image Processing," Applied Optics 50(2):170-176, Jan. 10, 2011.
(Continued)

*Primary Examiner* — Dave Czekaj
*Assistant Examiner* — Tsion B Owens
(74) *Attorney, Agent, or Firm* — Barry L. Davison; Davis Wright Tremaine LLP

(57) ABSTRACT

Provided are modular volume holographic imaging system (VHIS) endoscopic systems, comprising: an endoscope attachment module having a microscope objective lens, a single or cascaded compensated relay system configured to preserve an optical wavefront for use with a single or multiplexed volume hologram to select wavefronts originating from different object depths, and a system aperture; and a handle module configured to be reversibly attachable for operative communication with the endoscope attachment module, and having a beam splitter; a relay having adjustable spacing for object space focus compensation, and a single or multiplexed volume hologram suitable in operation to select wavefronts originating from different object depths, and wherein the handle module is further configured for operative communication with an illumination source and imaging optics. Preferably, an illumination module and an imaging module are configured to be in operative, reversibly attachable communication with the handle module. Flexible tip endoscopic embodiments are provided.

17 Claims, 22 Drawing Sheets

(51) Int. Cl.

| | | |
|---|---|---|
| *G03H 1/00* | (2006.01) | |
| *G03H 1/02* | (2006.01) | |
| *G03H 1/28* | (2006.01) | |
| *A61B 1/00* | (2006.01) | |
| *G02B 23/24* | (2006.01) | |
| *G03H 1/04* | (2006.01) | |
| *H04N 7/18* | (2006.01) | |

(52) U.S. Cl.
CPC ....... *G02B23/2446* (2013.01); *G02B 23/2469* (2013.01); *G03H 1/0248* (2013.01); *G03H 1/041* (2013.01); *G03H 1/0443* (2013.01); *G03H 1/0465* (2013.01); *G03H 1/28* (2013.01); *H04N 7/183* (2013.01); *G03H 2001/005* (2013.01); *G03H 2001/0436* (2013.01)

(56) References Cited

U.S. PATENT DOCUMENTS

| | | | |
|---|---|---|---|
| 7,158,228 B2 | 1/2007 | Psaltis | |
| 7,262,889 B2 | 8/2007 | Sun | |
| 9,295,375 B2* | 3/2016 | Shahinian | A61B 1/045 |
| 2005/0270609 A1 | 12/2005 | Chuang | |
| 2007/0241266 A1 | 10/2007 | Gweon | |
| 2008/0123069 A1* | 5/2008 | Wabra | G03F 7/70308 355/52 |
| 2009/0270683 A1 | 10/2009 | Farr | |
| 2010/0296178 A1* | 11/2010 | Genet | A61B 1/00188 359/754 |
| 2013/0258429 A1* | 10/2013 | Kostuk | G02B 5/32 359/9 |
| 2013/0271803 A1* | 10/2013 | Yao | G03H 1/12 359/10 |
| 2016/0025970 A1* | 1/2016 | Fukuyama | G02B 13/22 359/279 |

OTHER PUBLICATIONS

Castro, J.M., et al., "Confocal-Rainbow Volume Holographic Imaging System," Applied Optics, 50(10):1382-1388, Apr. 1, 2011.

Castro, J.M., et al., "Spatial-Spectral Volume Holographic Systems: Resolution Dependence on Effective Thickness," Applied Optics 50(7):1038-1046, Mar. 1, 2011.

Gelsinger-Austin, P.J., et al., "Optical Design for a Spatial-Spectral Volume Holographic Imaging System," Optical Engineering 43(4):043001-1-43001-5, Apr. 2010.

Li, Z., et al., "Volume Holographic Spectral Imaging," Proceedings of the SPIE 5694, Spectral Imaging: Instrumentation, Applications, and Analysis III, Mar. 31, 2005, pp. 33-40.

Liu, W., et al. "Real-Time Spectral Imaging in Three Spatial Dimensions," Optics Letters 27(10):854-856, May 15, 2002.

Luo, Y., et al., "Optimization of Multiplexed Holographic Gratings in PQ-PMMA for Spectral-Spatial Filters," Optics Letters 33(6):566-568, Mar. 15, 2008.

Luo, Y., et al., "Simulation and Experiments of Aperiodic and Multiplexed Gratings in Volume Holographic Imaging Systems," Optical Express 18(18):19273-19285, Aug. 30, 2010.

Oh, et al., "Theoretical Analysis of Curved Bragg Diffraction Images From Plane Reference Volume Holograms," Applied Optics 48(31):5984-5996, Nov. 1, 2009.

Sinha, A., and B. Barbastathis, "Broadband Volume Holographic Imaging," Applied Optics 43(27):5215-5221, Sep. 20, 2004.

Sinha, A., et al., "Volume Holographic Imaging in the Transmission Geometry," Applied Optics 43(7):1553-1551, Mar. 1, 2004.

Sun, W. and G. Barbastathis, "Rainbow Volume Holographic Imaging," Optics Letters 30(9):976-978, May 1, 2005.

International Search Report mailed Feb. 27, 2013, in International Patent Application No. PCT/US2012/061196, filed Oct. 19, 2012, 3 pages.

International Search Report mailed May 1, 2012, in International Patent Application No. PCT/US2011/053109, filed Mar. 29, 2012, 3 pages.

* cited by examiner

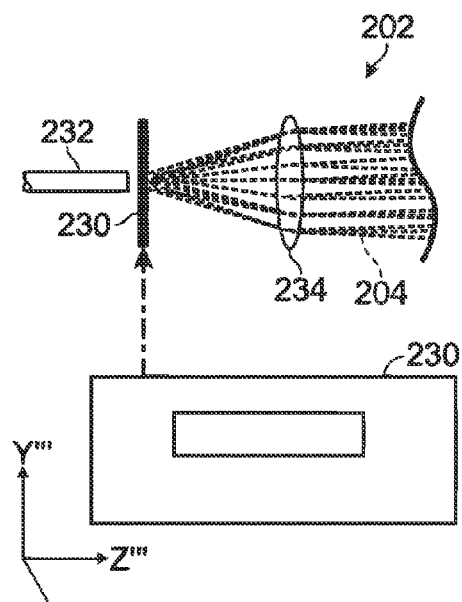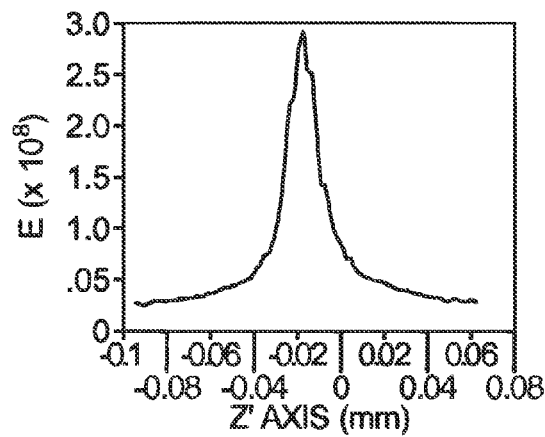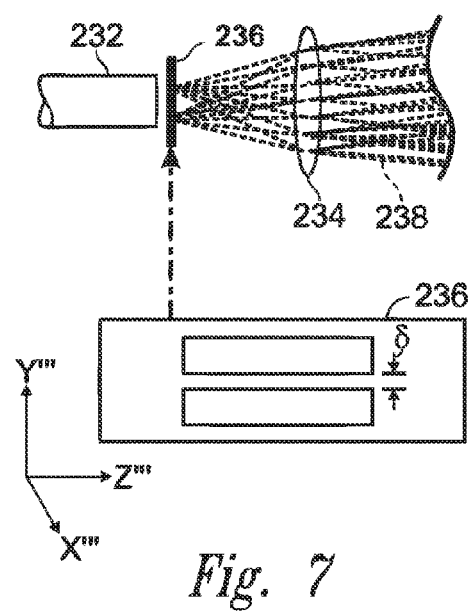
Fig. 5    Fig. 6
Fig. 7

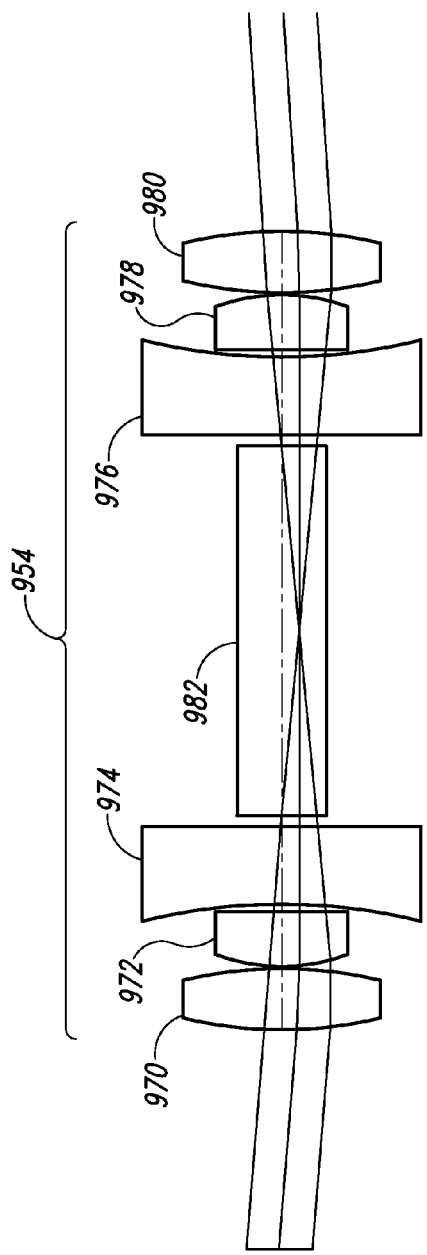
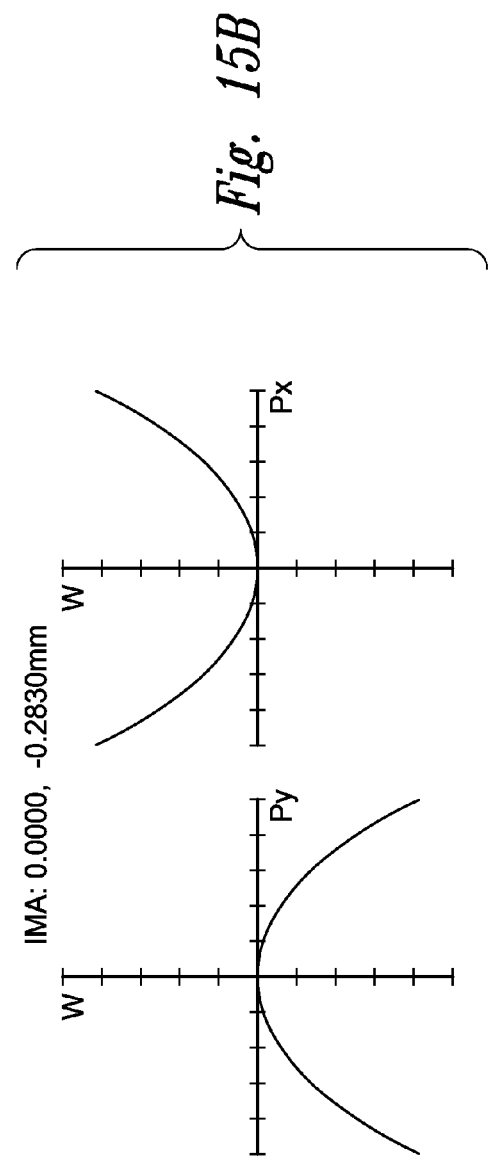

VOLUME HOLOGRAPHIC IMAGING SYSTEM (VHIS) ENDOSCOPE

CROSS-REFERENCE TO RELATED APPLICATIONS

This patent application is the United States national phase, under 35 U.S.C. §371, of International Patent Application No. PCT/US2012/061196, filed 19 Oct. 2012 and entitled "VOLUME HOLOGRAPHIC IMAGING SYSTEM (VHIS) ENDOSCOPE," which claims the benefit of priority to U.S. Provisional Patent Application Ser. Nos. 61/628,000 filed on Oct. 21, 2011 and entitled "VOLUME HOLOGRAPHIC IMAGING SYSTEM (VHIS) ENDOSCOPE," and 61/633,925 filed Feb. 21, 2012 and entitled "OPTICAL DESIGN FOR THE VOLUME HOLOGRAPHIC IMAGING SYSTEM (VHIS) ENDOSCOPE," all of which are hereby incorporated by reference in their entirety.

FEDERAL FUNDING ACKNOWLEDGEMENT

This invention was made with government support under Grant No R01 CA134424 awarded by the National Institutes of Health (NIH). The government has certain rights in the invention.

TECHNICAL FIELD

The present invention relates generally to holographic imaging systems, and more particularly to volume holographic imaging systems comprising use of a single or cascaded compensated relay system to preserve an optical wavefront for use with a single or multiplexed volume hologram to select wavefronts originating from different object depths, and in even more particular applications, this technique enables the implementation of an endoscopic version of the volume hologram imaging system.

BACKGROUND

Current Optical Microscopes are Limited to Ex-Vivo Imaging Applications

The standard volume holographic imaging system (VHIS) consists of two lenses and a highly selective, multiplexed volume hologram. Nominally, these elements are positioned as shown in FIGS. 1 and 11. This system will produce a projection of the axial position in the object for which the holographic grating is designed. More than one grating may be multiplexed in the hologram, so observation of multiple depths simultaneously is possible. Such a device is useful in observing the 3-dimensional structure of objects, and there is significant interest in using this type of device to better understand the nature of some cancers in vivo. Multiple laboratory prototypes have been built using this conceptual design, mainly in the form of microscopes. As with many optical microscopes, however, use of the instrument is limited to ex-vivo imaging studies due to the bulk of the instrument.

Recent Improvements in VHIS, while Impressive, have Nonetheless not Enabled Creation of a Hand-Held Version of the VHIS that would Provide for In-Vivo Imaging.

High resolution three-dimensional (3D) optical imaging instruments, such as confocal microscopes and optical coherence tomography systems, are important tools in biological and medical research. During the last decade, volume holographic imaging systems (VHISs) have been developed which use the wavefront selection properties of a volume hologram to select multiple images from respective multiple object depths. See W. Liu et al. "Real-time spectral imaging in three spatial dimensions," Opt. Lett. 27, 854-56 (2002); A. Sinha et al., "Volume holographic imaging in the transmission geometry," Appl. Opt. 43, 1533-51 (2004)(herein "Sinha I"); Z. Li et al., "Volume holographic spectral imaging," Proc. SPIE 5694, 33-40 (2005); A. Sinha et al., "Broadband volume holographic imaging," Appl. Opt. 43, 5215-5221 (2004)(herein "Sinha II"); Y. Luo, "Optimization of multiplexed holographic gratings in PQ-PMMA for spectral-spatial filters," Opt. Lett. 33, 566-68 (2008)(herein "Luo I"); P. J. Gelsinger-Austin et al., "Optical design for a spatial-spectral volume holographic imaging system," Opt. Eng. 49, 043001 (2010); Y. Luo, "Simulation and experiments of aperiodic and multiplexed gratings in volume holographic imaging systems," Opt. Express 18, 19273-19285 (2010) (herein "Luo II"); W. Sun et al., "Rainbow volume holographic imaging," Opt. Lett. 30, 977-978 (2005); and, Psaltis et al., U.S. Pat. No. 7,158,228, all of which are hereby incorporated by reference in their entirety. Such VHISs have achieved lateral and depth resolution of ~3 $\mu$m and ~12 $\mu$m, respectively, when using monochromatic illumination and standard lens components. Liu et al., Sinha I, Sinha II, Luo I, Gelsinger-Austin et al., and Lou II, id. However, a disadvantage of using a monochromatic source is that lateral scanning is required in order to capture the complete image field.

Using a broadband source has been proposed and implemented with the goal of avoiding mechanical scanning while maintaining the resolution achieved using monochromatic sources. However, in practice it has been observed that the utilization of a broadband illuminator dramatically reduces the depth sectioning capabilities of VHIS. Sinha II, Luo I, Gelsinger-Austin, Luo II and Sun et al., Id.

An approach to improve depth resolution that utilizes a rainbow illumination pattern produced by the diffraction of a broadband source on an external grating has been proposed. Sun et al., id., and Sun et al. U.S. Pat. No. 7,262,889 (the Sun '889 Patent) which is hereby incorporated by reference in its entirety. This type of VHIS configuration has been shown capable of improving the depth resolution to values >200 $\mu$m. There are limitations for improving depth resolution beyond that value using this configuration, because it requires accurately matching the wavefront of the external diffraction gratings (illumination hologram) and internal diffraction gratings (imaging hologram) and because there must inevitably be a finite angle between the optical axis of the illumination hologram and the optical axis of the imaging hologram.

The basic configuration of a VHIS 10 is illustrated in FIG. 1. The system (having coordinates x, y, z) consists of an objective lens 12, a volume hologram 14 placed in the Fourier plane of the objective lens 12, and a collection lens 16. The objective lens 12 receives light from an object 18 disposed in object space (denoted by coordinates x', y', z'), and the collection lens 16 forms a real image 20 of the object in image space (denoted by coordinates x", y", z"). The hologram 14 comprises a thick hologram having angle-multiplexed planar and spherical wave gratings having high angular and spectral selectivity. A broadband source is used to illuminate the object. A system of this type is disclosed in the Sun '889 Patent.

Because of the high selectivity, each grating, if illuminated with a monochromatic point source, would select a specific wavefront that originates at a corresponding depth from within object space. Multiplexing several gratings into the same volume allows mapping points from multiple depths in object space to distinct, corresponding locations on the image plane (x", y") in image space as shown by respective marginal rays 17 and 19. For each plane in object space the mapping is determined by two properties of the volume hologram 14: (1) its spatial degeneracy; and (2) its angular dispersion. Because of the first property, the wavefront of a point source at any position along the y' axis satisfies the Bragg phase-matching condition of the hologram 14 and therefore is diffracted to the collection lens 16. This diffraction is responsible for the y axis field of view (FOV) of the system The FOV along the spatial degeneracy axis y axis does not follow a straight line along the y' axis, as represented by the cylinder axis shown in FIG. 1. Rather, it follows hyperbolic curves such as $\delta\lambda_0$, $\delta\lambda_1$, $\delta\lambda_2$, $\delta\lambda_3$, $\delta\lambda_4$ and so forth, as illustrated in FIG. 3 and described in Castro et al., "Analysis of diffracted image patterns from volume holographic imaging systems and applications to image processing," Appl. Opt. 50, 170-176 (2011), hereby incorporated by reference in its entirety. The lateral resolution in the y axis depends mainly on the numerical aperture (NA) of the objective lens 12.

The angular dispersion of the hologram 14 and the spectral bandwidth of the readout source in image space, such as a CCD array, determine the FOV in the dispersive axis, that is, x axis. The lateral resolution along the x axis depends on the spectral selectivity of the hologram, which can be improved by optimizing its fabrication parameters. Luo I, Gelsinger-Austin et al., and Luo II, id., and Castro et al., "Resolution dependence on index modulation profile and effective thickness in volume holographic imaging systems," Appl. Opt. (1 Mar. 2011, Vol. 50, No. 7, pp. 1038-46), hereby incorporated by reference in its entirety. For a VHIS operating with monochromatic illumination, the depth selectivity depends on the NA of objective lens 12 and the angular bandwidth of the hologram 14.

VHIS prototypes using monochromatic sources have achieved lateral resolution of 2:5 µm and depth resolution of ~12 µm. Liu, id. However, a drawback is that in this configuration, scanning is required to capture the x axis FOV. However, when a broadband light source is utilized as an illuminator in the VHIS, the depth selectivity is essentially lost.

A VHIS 100 using multi-spectral, or "rainbow," illumination to improve the selectivity without requiring lateral scanning is illustrated in FIG. 2. This approach requires two sets of gratings and lenses: one to provide the rainbow illumination and the other for imaging. Thus, a beam of multi-spectral illumination 102 is applied to illumination hologram 104, which diffracts the multi-spectral light by different angles depending on the wavelength of the light, as shown at 106 by marginal rays 107 and 109. An illumination lens 108 then focuses light of different wavelengths to different locations in its image space. The image space of the illumination lens 108 is the object space 110 of an objective lens 112 that collects light from points in that object space, collimates it and illuminates an imaging hologram 114. The hologram 114 discrimination selects light from only one point in object space for a given wavelength as shown by marginal rays 111 and 113 and directs light 120 though a collection lens (not shown) to a corresponding unique point on a plane in image space.

The rainbow illumination is produced by the dispersive properties of the illumination hologram 104. Ideally, the illuminated plane 116 should overlap the object plane 118 along the complete FOV of both the illumination lens 108 and the objective lens 112. Also, the spectral dispersion produced by each set of optical elements should match. This ideal condition cannot be fully attained with the layout shown in FIG. 2. The challenge of dispersion-matching between gratings in the illumination hologram 104 and the gratings in the imaging hologram 114 limit the depth resolution not only in the optical axis but also over the complete FOV in the object plane. Even if that challenging condition could be satisfied, an overlap between the illuminated plane 116 and the object plane 118 is required. For imaging systems using an objective lens with NA>0:5, this latter condition is not attainable with external illumination and a thin grating with poor selectivity properties must be used. For example, FIG. 2 shows that there is a tilt angle, $\epsilon$, between the object plane and the illuminated plane. This angle, which takes values of ~60° for lenses with NA ¼ 0:5, reduces significantly the region in which the object and the illuminated plane overlap.

Recently, a new type of VHIS, referred to as "confocal rainbow volume holographic imaging system (CR VHIS) that provides for depth sectioning of an object, eliminates the need for a mechanical scanning apparatus to cover the FOV of the system, provides high lateral and depth resolution, and provides for a high image contrast ratio has been described (see PCT/US2011/053109; published as WO 2012/040639 A2; incorporated by reference herein it its entirety). Essentially, CR VHIS uses the same light path to illuminate an object with multi-spectral light as to image the object.

In view of the foregoing, however, there has been an unmet need for a hand-held version of the VHIS (or of CR VHIS) so that in-vivo imaging may be possible, with data comparable to the bench-top VHIS microscope.

SUMMARY

What is presented herein are novel volume Holographic Imaging System (VHIS) Endoscopes, which use a single or cascaded-compensated relay system to preserve an optical wavefront for use with a single or multiplexed volume hologram to select wavefronts originating from different object depths. This technique enables the implementation of an endoscopic version of the volume hologram imaging system. Both rigid flexible endoscopes are provided herein according to aspects of the invention. While rigid VHIS endoscopic instruments can be effectively used in minimally invasive clinical procedures, more flexible VHIS endoscopic embodiments provide even more clinical utility.

Provided are modular volume holographic imaging system (VHIS) endoscopic systems, comprising: an endoscope attachment module having a microscope objective lens, a single or cascaded compensated relay system configured to preserve an optical wavefront for use with a single or multiplexed volume hologram to select wavefronts originating from different object depths, and a system aperture; and a handle module configured to be reversibly attachable for operative communication with the endoscope attachment module, and having a beam splitter; a relay having adjustable spacing for object space focus compensation, and a single or multiplexed volume hologram suitable in operation to select wavefronts originating from different object depths, and wherein the handle module is further configured for operative communication with an illumination source and imaging optics. Preferably, an illumination module and an imaging module are configured to be in operative, reversibly attachable communication with the handle module. Flexible tip endoscopic embodiments are provided.

Preferred Volume Holographic Imaging System (VHIS) Endoscopic System Embodiments Certain aspects provide a modular volume holographic imaging system (VHIS) endoscopic system, comprising: an endoscope attachment module having an observing end and a distal attachment end, a microscope objective lens positioned at the observing end, a single or cascaded compensated relay system having one or a plurality of pupil relays positioned between the objective lens and the distal attachment end and configured to preserve an optical wavefront for use with a single or multiplexed volume hologram to select wavefronts originating from different object depths, and a system aperture with pupil positioned between the objective lens and the one or the plurality of pupil relays; and a handle module configured to be reversibly attachable for operative communication with the endoscope attachment module, and having a beam splitter, a relay having adjustable spacing for object space focus compensation, and a single or multiplexed volume hologram suitable in operation to select wavefronts originating from different object depths, and wherein the handle module is further configured for operative communication with an illumination source and imaging optics.

Particular aspects further comprise an illumination module in operative communication with the handle module, and having a light source, and a source lens 664, and optionally having an illumination hologram, and/or a relay, wherein the source lens is operatively positioned between the light source and the illumination hologram, which is operatively positioned between the source lens and the relay, and wherein the illumination module is optionally configured as a module that is reversibly attachable to the handle module.

In certain aspects, the illumination module comprises a Koehler illumination system that provides broadband illumination, and/or a confocal rainbow illumination system configured within the endoscopic system for provide for rejecting out-of-plane scattering sources. In certain aspects, the illumination module comprises a confocal rainbow illumination system configured within the system to disperse monochromatic illumination across the object field, and wherein the dispersed light is matched angularly to the imaging hologram inside the handle module to provide an optical sectioning effect capable of eliminating energy from out-of-plane scattering sources in the object.

Certain aspects, further comprise an imaging module, in operative communication with the handle module, and having a collector lens, configured within the imaging module to provide for adjustable spacing for image space compensation, and wherein imaging module is optionally configured as a module that is reversibly attachable to the handle module.

Certain aspects, further comprise an illumination module configured to be in operative, reversibly attachable communication with the handle module, and having a light source, and a source lens, and optionally having an illumination hologram, and/or a relay, wherein the source lens is operatively positioned between the light source and the illumination hologram, which is operatively positioned between the source lens and the relay; and imaging module configured to be in operative, reversibly attachable communication with the handle module, and having a collector lens, configured within the imaging module to provide for adjustable spacing for image space compensation. In particular embodiments, the endoscope attachment module comprises a plurality of relay stages configured to produce an image of the system aperture at the output (distal attachment end) of the endoscope attachment module. In certain aspects, the endoscope attachment module comprises: a microscope objective; an objective-proximal compensating pupil relay; and a series of modular pupil relays having a combination of bi-convex, planoconvex, and plano-concave lens elements. In particular aspects, a first, objective-proximal, relay stage (compensating pupil relay) is specifically designed and configured to compensate the off-axis aberrations of microscope objective (e.g., an aspheric singlet microscope objective), and wherein a plurality or series of further distal relay stages are corrected for infinite conjugates and configured to be modular. In particular aspects, the plurality or series of further distal modular relay stages (modular pupil relays) are configured to propagate a nominally planar wavefront from the pupil aperture through the system. In certain aspects, the modular pupil relays are corrected for infinite conjugates, and each employ a centrically located Hopkins rod to extend the length of the endoscope attachment module, and wherein the modular pupil relays are configured to be monochromatic at each field angle. In particular aspects, field curvature is removed as an aberration by slightly curving the object plane, and wherein correction of monochromatic aberrations is achieved by using a combination of bi-convex, planoconvex, and plano-concave lens elements. In particular aspects, first and last bi-convex lenses determine spherical aberration of the system, wherein adjusting their radii provides for tuning of the spherical aberration, and wherein inner planoconvex lenses and determine system astigmatism, wherein adjusting their radii provides for tuning of system astigmatism, and wherein negative plano-concave lens elements introduce negative spherical aberration and astigmatism to balance the respective positive elements in the system, and reduce the overall field curvature component of the Seidel sum.

In certain aspects, the endoscope attachment module and the handle module are configured as a flexible endoscopic tip, and additionally comprise, in operative communication with the flexible endoscopic tip, a camera, a flexible cable and a monitor, wherein the flexible cable is suitable to carry both electrical signals from the camera, and further comprises optical fiber suitable for illumination of the tissue sample through the flexible endoscopic tip.

In preferred aspects of endoscopic devises disclosed herein, the endoscope attachment module comprises; an objective module having the microscope objective lens; and a relay module having the single or cascaded compensated relay system having one or a plurality of pupil relays, and wherein microscope objective is independently aberration-corrected from the rest of the system. In certain embodiments, the objective module comprises a diode-collimating asphere as a microscope objective lens, wherein astigmatism is correctable by equally adjusting the radii of the inner plano-convex lens elements of the compensating pupil relay, and wherein coma is correctable by the asymmetry of the first and last lens elements of the compensating pupil relay, and tunable by adjusting the air space between a second plano-concave lens and the subsequent plano-convex lens of the compensating pupil relay.

Additional aspects of the above, comprise a common-path broadband light source and source lens to provide illumination at the object plane, wherein the source is positioned so that the source and object planes are confocal, and wherein the hologram disperses light from the source plane such that each point along the dispersive axis of the object plane is essentially monochromatically illuminated, creating an optical sectioning effect with a characteristic optical section thickness.

It is to be understood that this summary is provided as a means for generally determining what follows in the drawings and detailed description, and is not intended to limit the scope of the invention. Objects, features and advantages of the invention will be readily understood upon consideration of the following detailed description taken in conjunction with the accompanying drawings.

BRIEF DESCRIPTION OF THE DRAWINGS

FIG. 5 is an illustration of the structure and operation of a first embodiment of a multi-spectral illuminator for use in the system of FIG. 4.

FIG. 6 is a representative graph of energy propagated through the system of FIG. 4 as a function of position of the object surface along the optical axis of the system.

FIG. 7 is an illustration of the structure and operation of a second embodiment of a multi-spectral illuminator for use in the system of FIG. 4.

FIGS. 15A and B illustrate an exemplary design configuration of a modular pupil relay (as suitable for use in the endoscope attachment (barrel) module of FIG. 14), which is designed for infinite conjugates, and employs a Hopkins rod 982 in the middle to extend the length of the design.

DETAILED DESCRIPTION OF EMBODIMENTS OF THE INVENTION

Figure 1:
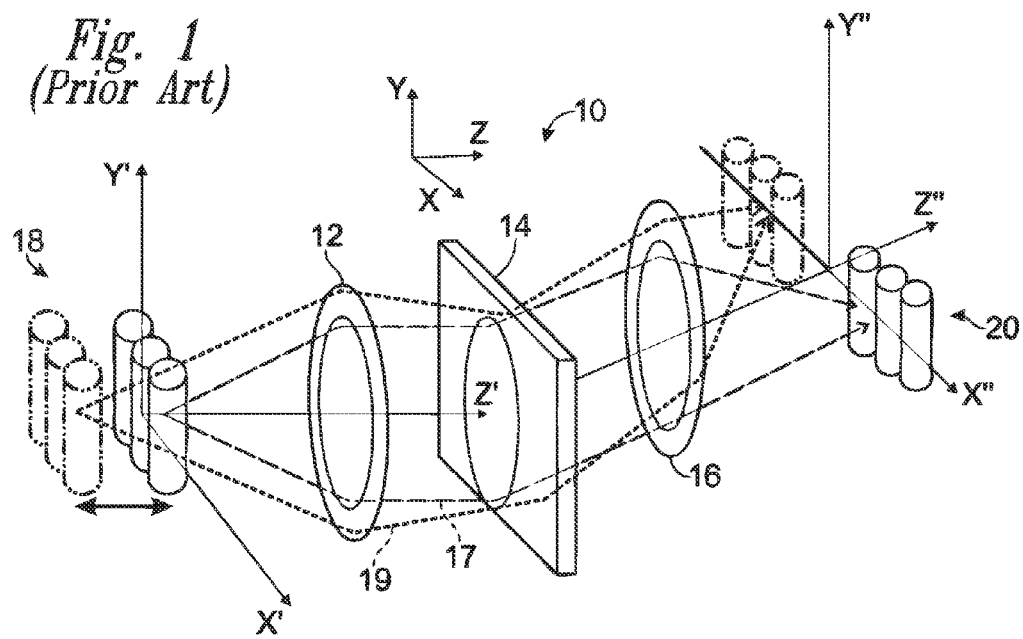
FIG. 1 is an illustration of the structure and operation of a first prior art volume holographic imaging system.

The present invention will be readily understood by the following detailed description in conjunction with the accompanying drawings. To facilitate this description, like reference numerals designate like structural elements. In the following description many details are set forth to provide an understanding of the disclosed embodiments of the invention. However, upon reviewing this disclosure, it will become apparent to one skilled in the art that not all of the disclosed details may be required to practice the claimed invention and that alternative embodiments might be constructed without departing from the principles of the invention.

I. Confocal Rainbow Volume Holographic Imaging" (CF VHI)

To provide a VHIS which enables depth sectioning of an object, eliminates the need for a mechanical scanning apparatus to cover the FOV of the system and provides high lateral and depth resolution, a system is disclosed which uses the same light path to illuminate an object with multi-spectral light as to image the object. This approach is referred to herein as "confocal rainbow volume holographic imaging" (CF VHI) and such a system is referred to herein as a "confocal rainbow holographic imaging system" (CR VHIS). This approach overcomes the need to mechanically scan along the non-degenerate lateral axis in object space, the difficulty of matching dispersive characteristics of separate illumination and imaging holograms that have different optical axes, and the lack of FOV overlap produced by separate illumination and imaging holograms that have different optical axes.

Figure 4:
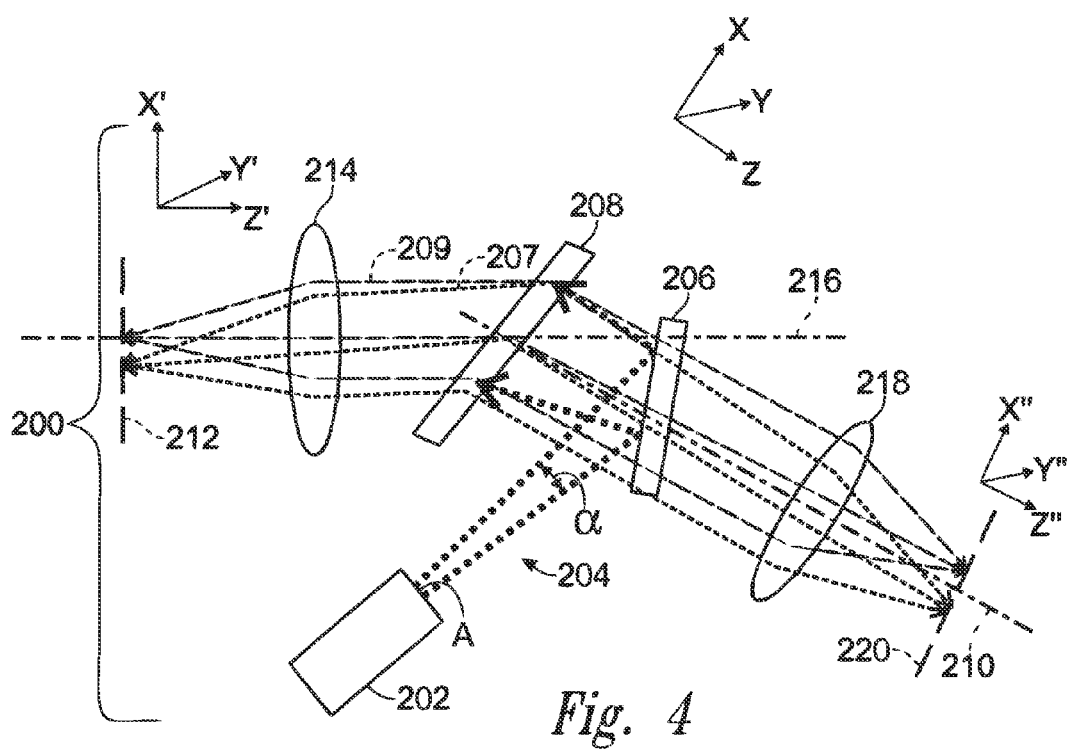
FIG. 4 is an illustration of the structure and operation of a first embodiment of a confocal-rainbow volume holographic imaging system according to the present invention.

A first embodiment 200 of a CR VHIS is shown in FIG. 4. In this embodiment a multi-spectral illuminator 202 produces a broad band illumination beam 204 of light with a non-symmetric limited angular spectrum as will be explained further hereafter. A beam splitter 206 reflects that illumination beam toward a volume hologram 208 that serves as both an illumination hologram and an imaging hologram. The hologram 208 is tilted at selected angles $X_\theta$ and $Y_\beta$ to the optical axis 210 in the system space (denoted by coordinates X, Y, Z) to maximize the FOV and minimize stray light reflections. Emitting area A and angle α of the light beam illuminator 202 are designed to fill both the aperture of the hologram 208 and its acceptance angle after being reflected by the beam splitter.

The hologram 208 disperses the multi-spectral light from beam 204 at different angles along the X' axis of the object space (denoted by X', Y', Z'), which angles are a function of the wavelength of the light, as shown by marginal rays 207 and 209. The light is focused to points on a plane 212 along the X' axis in object space by objective lens 214 having a common illumination and imaging optical axis 216. Light reflected from a point on an object along plane 212 in object space travels back through objective lens 214, where it is substantially collimated, and through the hologram 208 along the same path it followed to get to the object from the beam splitter 206. This reflected light passes through the beam splitter to collection lens 218, which focuses it to a spot on image plane 220. The spot to which the light is focused depends on several things: the wavelength λ of the light; the depth along Z' of the plane in object space; and the positions of the point along X' and Z' in object space.

Thus, in the CR VHIS 200 light passes through the hologram 206 and the objective lens 214 twice: once to produce the illumination and again to form the image. The double light pass through the objective lens and the hologram results in a spatial filtering effect comparable to that found in a slit confocal microscope. Light from the object corresponding to wavefronts not recorded in the hologram is rejected.

Turning now to FIG. 5, the illuminator 202 includes a mask 230 for placement behind a multi-spectral light source, such as fiber bundle 232 emitting multi-spectral light. When using a one-grating hologram the mask has only one aperture as indicated in FIG. 5. The mask has a rectangular aperture with asymmetrical shape to match the dispersive (X) axis and degenerate (Y) axis of the image formed by the hologram. The aperture is selected to limit the size of illumination to reduce reflective noise in the system. The mask 230 is followed by an output lens 234 that couples the output light 204 to the hologram 208 in FIG. 4 and matches the multi-spectral light source to the angular bandwidth and size of the hologram.

To achieve depth sectioning, a plurality of gratings must be present in the hologram 208 and the illuminator employs a mask having a corresponding plurality of apertures. As an example, referring to FIG. 7, for a two-grating multiplexed hologram, a mask 236 with two apertures is used to produce separate beams in the output light 238 that activate two respective gratings in the hologram. Assuming an angular separation δ between gratings, the separation h of the apertures is given by $h \propto f_1 \tan(\delta)$, where $f_1$ is the focal light of lens 234. For a hologram having more than two gratings, which is needed to section the object at more than two respective depths, each mask aperture must be separated from its nearest neighbors by δ.

Figure 2:
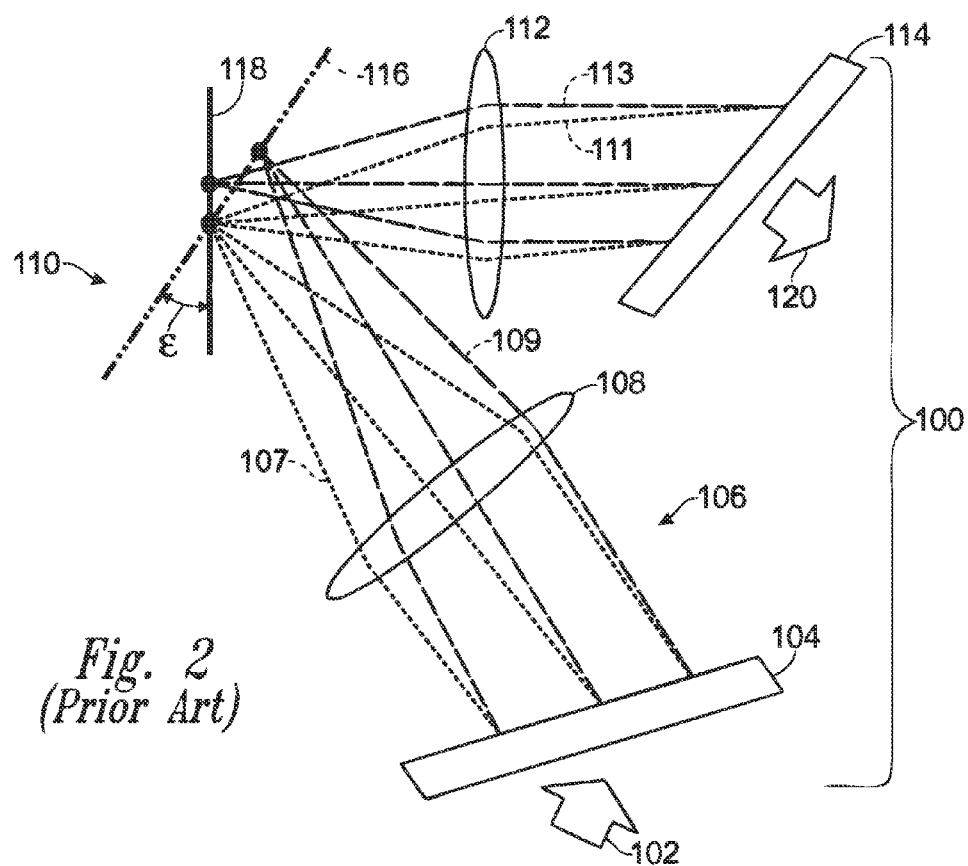
FIG. 2 is an illustration of the structure and operation of a second prior art volume holographic imaging system.
Figure 3:
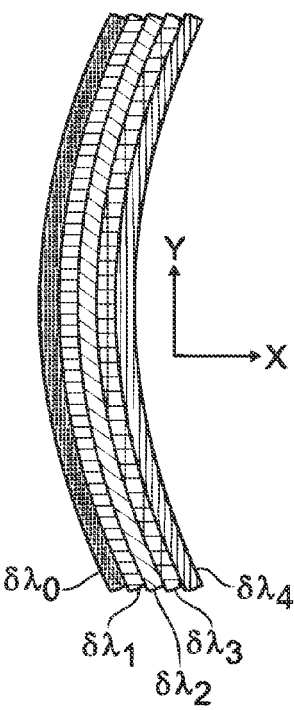
FIG. 3 is an illustration of a representative image of a band of multi-spectral illumination light produced on a focal plane of an objective lens in a volume holographic imagining system.

As in the case of the prior art VHIS shown in FIG. 2, the illumination light produces a rainbow pattern as shown in FIG. 3 on an object plane such as plane 212 in FIG. 4. In FIG. 3 the spread of each wavelength band of the source spectrum is represented as a slit. The width of each slit (color), $\delta\lambda_0$, $\delta\lambda_1$, $\delta\lambda_2$ and so forth, which is exaggerated in FIG. 3, depends on the angular bandwidth of the hologram 208 and, therefore, on the effective thickness and index modulation profile of the hologram. The diffractive pattern shape follows the function F(x', y', λ, K). This function represents a set of conic curves, where x' and y' denote the position in the object plane, λ is the wavelength illuminating this position, and K is the grating vector the corresponding grating vector of the hologram 208. The function F(x', y', λ, K) can be derived from the Bragg condition, as explained in Castro, et al., supra, and also from the Born approximation, as explained in Oh et al., "Theoretical analysis of curved Bragg diffraction images from plane reference volume holograms," Appl. Opt. 48, 5984-5996 (2009), hereby incorporated by reference in its entirety. In most cases the diffractive field forms hyperbolic patterns. For a hologram 208 with negligible angular bandwidth, there is only one curve for each λ. However, in practice, there is a finite width for each color, which is in general one of the main limiting factors in all VHIS configurations.

By using the double pass optics, greater depth resolution may be achieved. This is shown by experimental results shown in FIG. 6 wherein the energy E captured by in the image is plotted as a function of the Z' axis in object space.

A CR VHIS requires careful design to minimize undesired reflection noise from the beam splitter 206 and the hologram surface 208. To minimize the specular reflection of the source to the detector, the hologram must be tilted around the x axis (β>0) to redirect reflected light out of the imaging path. Although the precise value of this rotation depends on the layout of the system, simulation and experimental results suggest β~10° to reduce this reflection. In addition, the illumination aperture size, A, and emitting angles, d, must be designed to fill the aperture of the hologram, as well as the hologram angular acceptance range, in order to illuminate the entire field of view efficiently. Descriptions of simulated and actual experimental results for CR VHISs can be found in Castro et al., "Confocal-rainbow volume holographic imaging system," App. Opt., Vol. 50, No. 10/1 (April 2011), hereby incorporated by reference in its entirety.

Figure 8:
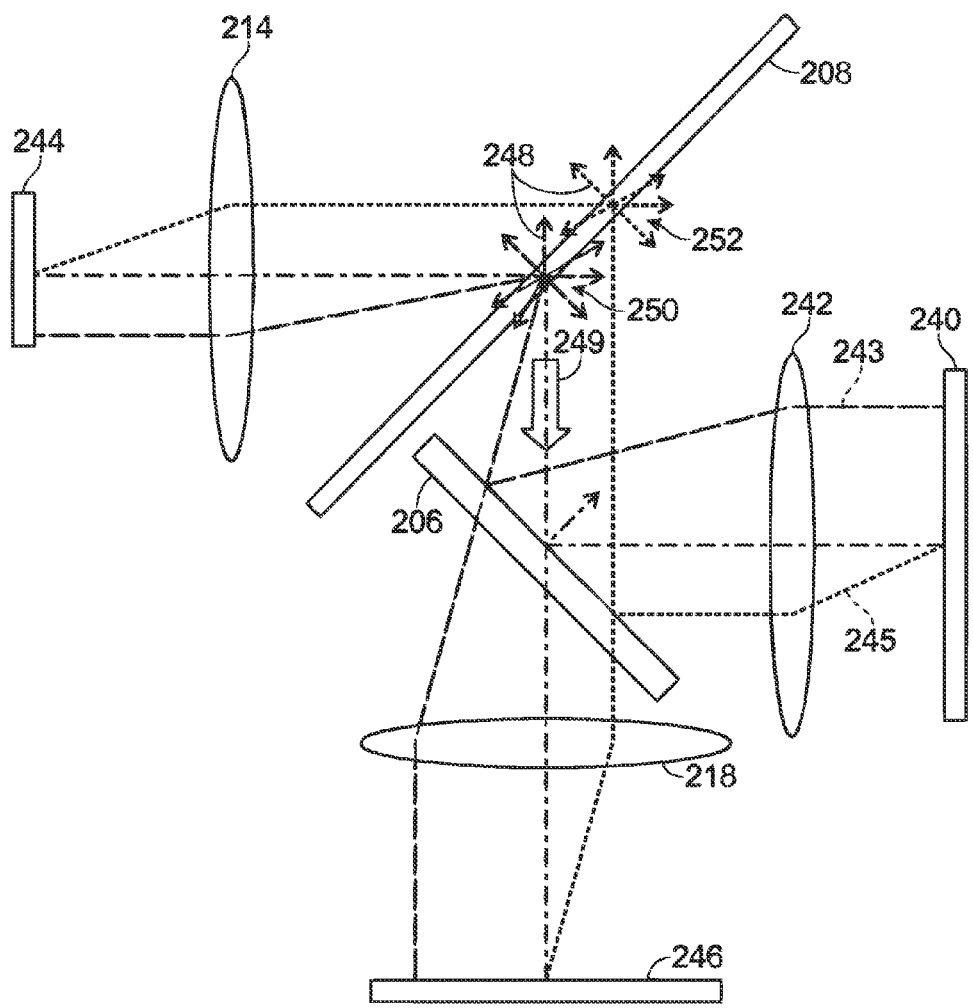
FIG. 8 is an illustration of a system of the type illustrated in FIG. 4 wherein light scattered by the hologram is illustrated.

A potential problem with any VHIS is that surface defects and bulk material imperfections in the volume hologram can produce unwanted random scattering that leads to low image contrast, that is, a low signal-to-noise ratio. This is illustrated in a CR VHIS by FIG. 8, where a simplified illuminator is represented by multi-spectral source 240 and lens 242, an object 244 is shown in object space, and an image detector 246, such as a CCD camera, is shown in image space. Light propagates through the system as shown by marginal ray 243 and principal ray 245. Light 248 that is randomly scattered by the hologram both when illumination light passes through it and when image light passes through it is illustrated at points 250 and 252. Much of that scattered light 249 finds its way to the image detector 246 because the illumination light and the imaging light share the same path.

Figure 9:
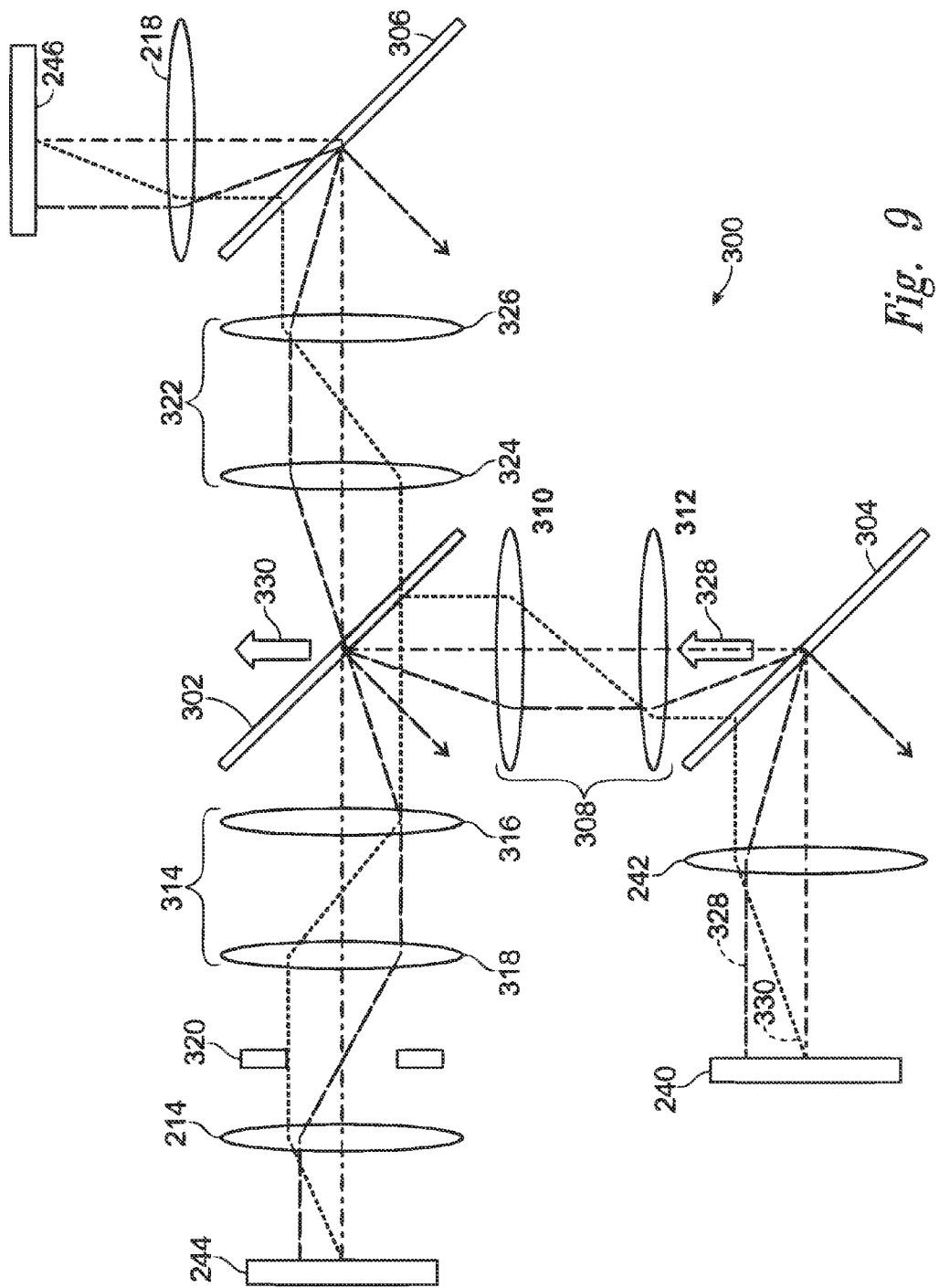
FIG. 9 is an illustration of a second embodiment of a confocal-rainbow volume holographic imaging system according to the present invention wherein two holograms are used to reduce scattering noise.

To reduce the amount of scattered light that makes it to the image detector, the imaging and illumination paths can be separated in a way that directs most of the scattered light away from the image detector, yet retains the advantages of a CR VHIS. A second embodiment 300 of the invention that produces this result is shown in FIG. 9. As in FIG. 8, an illuminator is represented by source 240 and lens 242, an object 244 is disposed in object space, and an image detector 246 is disposed in image space. However, in this case a beam splitter 302 is disposed between the object and two matched holograms 304 and 306. Hologram 304 is in the illumination path and hologram 306 is in the image path. Both holograms have identical construction to ensure that Bragg matching will occur across the entire FOV.

In this case a first relay 308 with unity magnification is disposed between the illumination hologram 304 and the beam splitter 302. The relay 308 comprises lens 310 and lens 312. A second relay 314, comprising lens 316 and lens 318, is disposed between the objective lens 214 and the beam splitter 302. Aperture stop 320 is disposed between objective lens 214 and relay 314 to establish the pupil of the objective lens system where the beam splitter is positioned. A third relay 322, comprising lens 324 and lens 326, is disposed between the beam splitter 302 and the imaging hologram 306. These relays enable the beam splitter to be placed at the pupil plane, which serves to create two distinct paths for illumination and imaging. Light propagates through the system as shown by marginal ray 328 and principal ray 330.

It can be seen that in this case, light 328 that is strongly scattered by the illumination hologram and light 330 that is strongly scattered by the imaging hologram is directed away from the imaging path.

Figure 10:
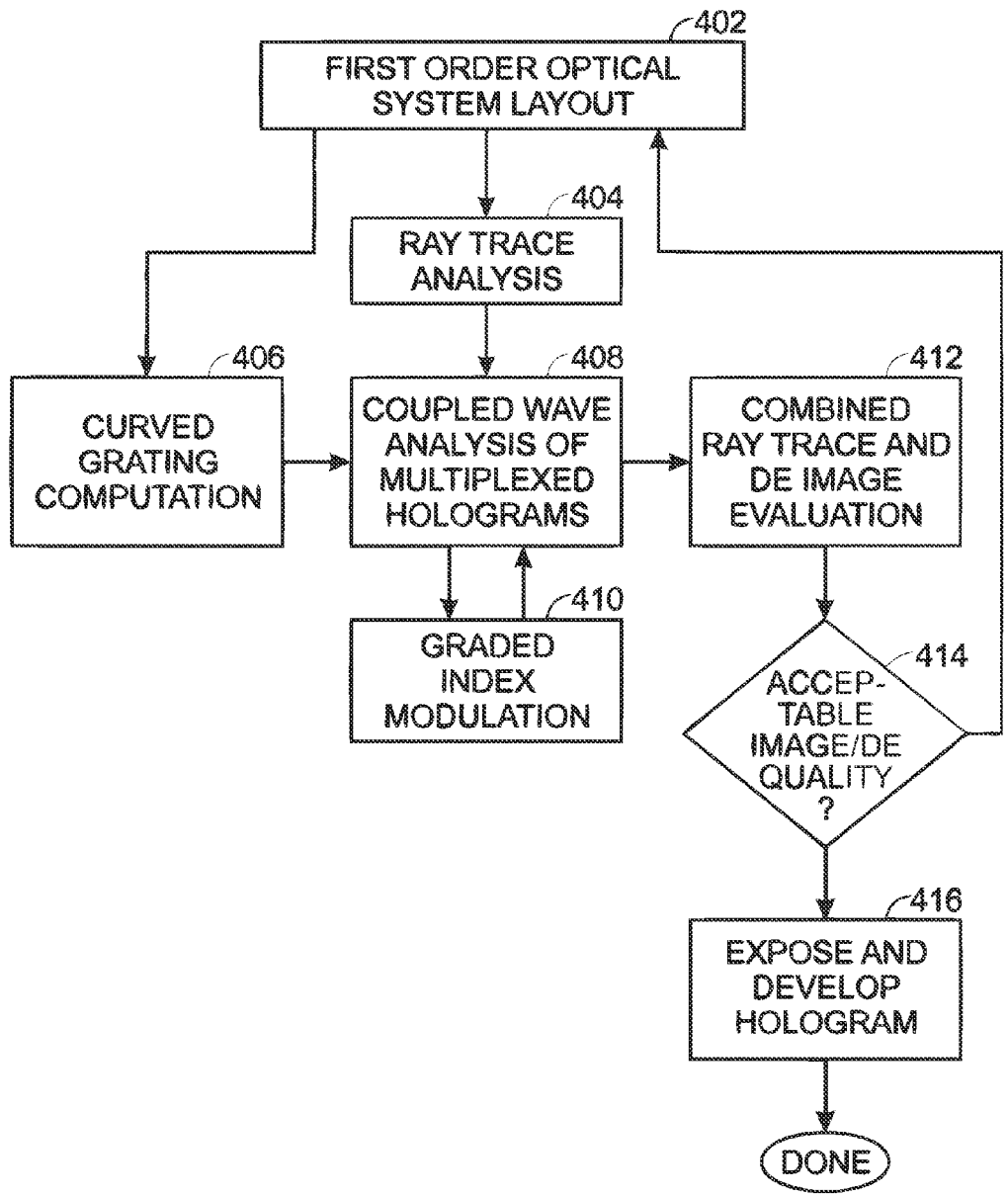
FIG. 10 is a flow chart representing the steps of a method for producing a volume hologram for use in a confocal rainbow volume holographic imaging system according to the present invention.

A method for producing a suitable hologram 208, 304 and 306 is illustrated in the flow chart in FIG. 10. Initially, at step 402, a first order optical design is configured to provide the basic layout of the imaging system. In step 404, the output from the first order design is used in a ray trace analysis of the system and, in parallel step 406, to compute the curvature of the grating vector across the aperture of the hologram. In step 408, localized grating vectors and incident ray directions are used in conjunction with coupled wave analysis to determine the diffraction efficiency at different locations on the hologram aperture and the direction of the diffracted beam from the localized coordinates. In step 410, the refractive index is modulated to determine its effect on the diffraction efficiency. The combined ray trace and diffraction efficiency (DE) values from each location on the aperture are used in step 412 to determine the image properties. The image result is evaluated in step 414 to decide if the system performance is acceptable. If so, the parameter of the hologram are used in step 416 to expose photosensitive polymers based on those parameters, and the polymer is developed to obtain the hologram.

Preferred Confocal Rainbow Volume Holographic Imaging" (CF VHI) Embodiments

Particular embodiments provide a holographic imaging system, comprising: a volume hologram having a front and a back and at least one diffraction grating formed therein; an objective lens having a front and a back and being disposed in front of the hologram so as to perform an optical transformation between a point on a surface in front of the objective lens corresponding to said diffraction grating and a beam propagating between the back of the objective lens and the front of the hologram; a collection lens having a front and a back and being disposed in back of the hologram so as to perform an optical transformation from beam propagating from the back of the hologram to the front of the collection lens and to a point in back of the collection lens; and a multi-spectral illuminator disposed with respect to the hologram so as to provide an illumination beam of light coupled to the back of the hologram to produce multiple diffracted beams of light at the front of the hologram corresponding wavelengths of light in the illumination beam which are focused by the objective lens to respective different positions on the surface in front of the objective lens corresponding to said diffraction grating. Certain embodiments comprise a beam splitter disposed between the back of the hologram and the illuminator so as to direct light from the illuminator toward the back of the hologram and to direct light from the back of the hologram to the collection lens. In particular embodiments, the illuminator comprises a multi-spectral light source and an illuminator lens for transforming light from the light source to the illumination beam of light coupled to the back of the hologram. In certain embodiments, the illuminator further comprises a mask having at least one rectangular aperture disposed between the multi-spectral light source and the illuminator lens. In certain aspects, the hologram has multiple diffraction gratings formed therein and the mask has corresponding multiple apertures formed therein so that light transmitted through each aperture converges to a point on a corresponding distinct plane in front of the objective lens and each image of point in front of the objective lens is formed at a unique location on the back focal plane of the collection lens. Certain aspects additionally comprise an image detector disposed at the back focal plane of the collection lens so as to detect images of points on an object disposed in front of the objective lens. In certain embodiments, the illuminator comprises a multi-spectral light source and an illuminator lens for transforming light from the light source to the illumination beam of light coupled to the back of the hologram. In particular aspects, the illuminator further comprises a mask having at least one rectangular aperture disposed between the multi-spectral light source and the illuminator lens. In certain embodiments, the hologram has multiple diffraction gratings formed therein and the mask has corresponding multiple apertures formed therein so that light transmitted through each aperture converges to a point on a corresponding distinct plane in front of the objective lens and each image of point in front of the objective lens is formed at a unique location on the back focal plane of the collection lens. In particular aspects, the hologram has multiple diffraction gratings formed therein and so that light in the illumination bean originating from different lateral positions converges to respective points on a corresponding distinct parallel planes in front of the objective lens. Certain aspects comprise an image detector disposed at the back focal plane of the collection lens so as to detect images of points on an object disposed in front of the objective lens. Certain aspects comprise an image detector disposed at the back focal plane of the collection lens so as to detect images of points on an object disposed in front of the objective lens.

Certain aspects provide a holographic imaging system, comprising: an objective lens system having a front, a back, a first optical axis, and a pupil disposed in back of the objective lens system; a collection relay lens system having a front and a back and sharing the first optical axis; a collection lens having a front and a back; an imaging volume hologram having one or more diffraction gratings formed therein disposed between the collection lens and the collection relay lens system at a point on the first optical axis conjugate to the location of the pupil of the objective lens system on the first optical axis and at the front focal point of the collection lens; an illumination relay lens system having a front and a back and a second optical axis intersecting the first optical axis at a non-zero angle; an illumination lens having a front and a back; an illumination volume hologram disposed between the illumination lens and the illumination relay lens system at a point on the first second optical axis conjugate to the location of the pupil of the objective lens system on the first optical axis and at the back focal point of the illumination lens, the illumination volume hologram having diffraction gratings formed therein that are substantially identical to the diffraction gratings formed in the imaging hologram; and a beam splitter disposed at the intersection of the first optical axis and the second optical axis so as to reflect light from the illumination relay lens system toward the objective relay lens system and to pass light from the objective relay lens system to the collection relay lens system so that when a source of multi-spectral light is disposed at the front focal point of the illumination lens and an object is placed in front of the objective lens, points on the object that are illuminated by light from the multi-spectral source will be imaged at the back focal plane of the collection lens, while most light that is diffusely scattered by the illumination hologram and the imaging hologram will be directed away from the back focal plane of the collection lens by the beam splitter. In certain aspects, the objective lens system comprises an objective lens having a front and a back, an objective relay lens system in back of the objective lens, and an aperture stop disposed between the objective lens and the objective relay lens system so as to establish the pupil of the objective lens system. Particular embodiments further comprise a multi-spectral light source disposed at the front focal point of the illumination lens and a mask having at least one rectangular aperture disposed between the multi-spectral light source and the illumination lens. In certain aspects, the first and second holograms have multiple diffraction gratings formed therein and the mask has corresponding multiple apertures formed therein so that light transmitted through each aperture converges to a point on a corresponding distinct plane in front of the objective lens and each image of point in front of the objective lens is formed at a unique location on the back focal plane of the collection lens. In particular embodiments, the hologram has multiple diffraction gratings formed therein so that illumination light originating from different lateral positions converges to respective points on corresponding distinct parallel planes in front of the objective lens system. Certain aspects further comprise an image detector disposed at the back focal plane of the collection lens so as to detect images of points on an object disposed in front of the objective lens system. Certain aspects comprise an image detector disposed at the back focal plane of the collection lens so as to detect images of points on an object disposed in front of the objective lens system.

Additional aspects provide a method for making a thick hologram for use in an imaging system, comprising configuring a first order confocal rainbow holographic imaging system; performing a ray trace analysis of the first order optical system to compute the required curvature of the grating vector across the aperture of the hologram; determining the diffraction efficiency and the diffracted ray direction at a plurality of locations on the hologram aperture using corresponding localized grating vectors, corresponding ray directions from the ray trace analysis, coupled wave analysis; and determining properties of the image created by the optical system based on the ray directions and diffraction efficiencies at the plurality of locations on the hologram aperture. The steps may be repeated with different hologram refractive index modulations and evaluating the acceptability of the image properties until acceptable image performance is achieved.

According to particular aspects, and in the spirit and scope of the present invention, the above-described teachings relating to confocal rainbow volume holographic imaging" (CF VHI) are optionally applicable to the volume holographic imaging system (VHIS) endoscopic embodiments disclosed herein below.

II. Volume Holographic Imaging System (VHIS) Endoscope

Particular aspect of the present invention provide a volume holographic imaging system (VHIS) endoscope, comprising use of single or cascaded-compensated relay system to preserve an optical wavefront for use with a single or multiplexed volume hologram to select wavefronts originating from different object depths. This technique enables the implementation of an endoscopic version of the volume hologram imaging system.

Figure 11:
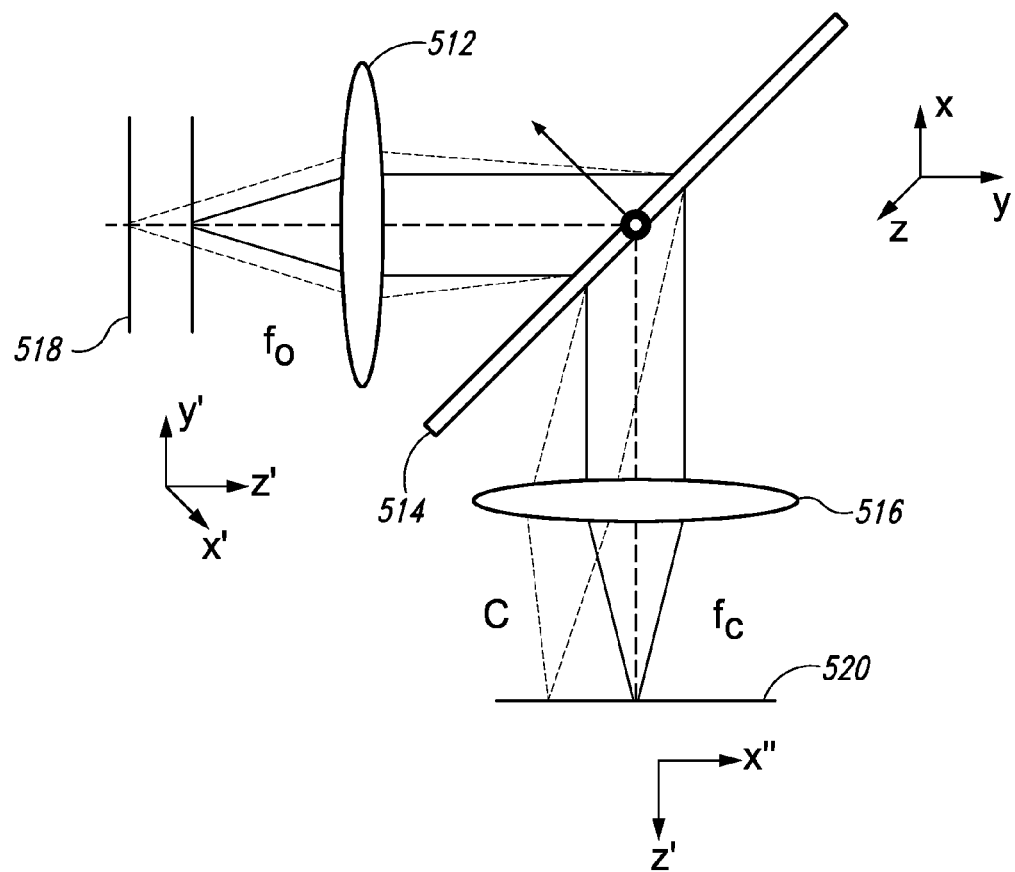
FIG. 11 is an illustration of the structure and operation of a second prior art volume holographic imaging system consisting of two lenses and a volume holographic grating, providing an instrument which can observe two axial positions simultaneously by laterally distributing them across the image plane
Figure 11A:
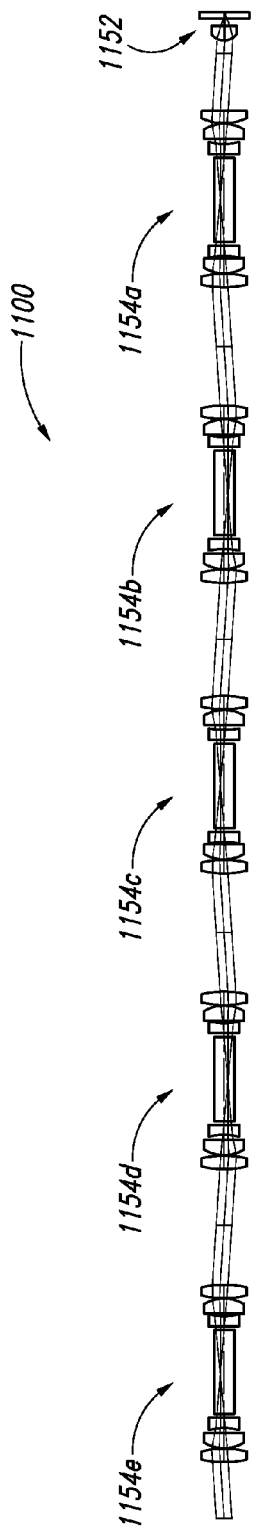
Figure 11B:
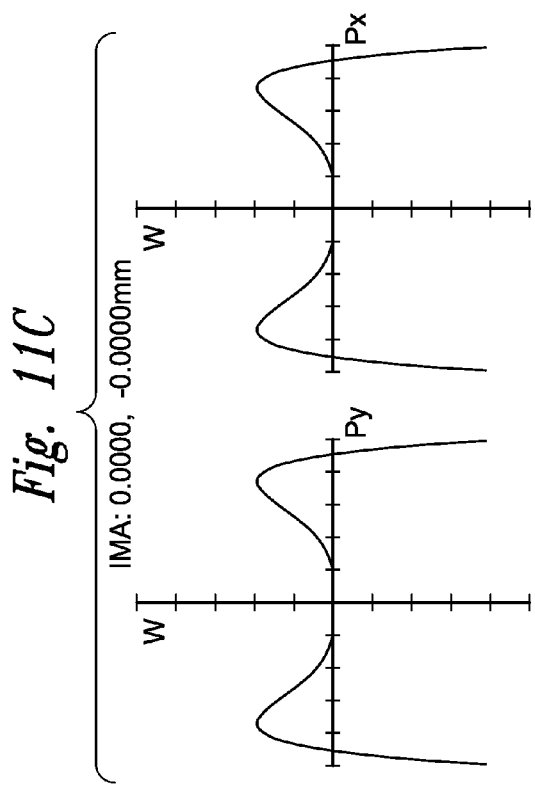
Figure 11C:
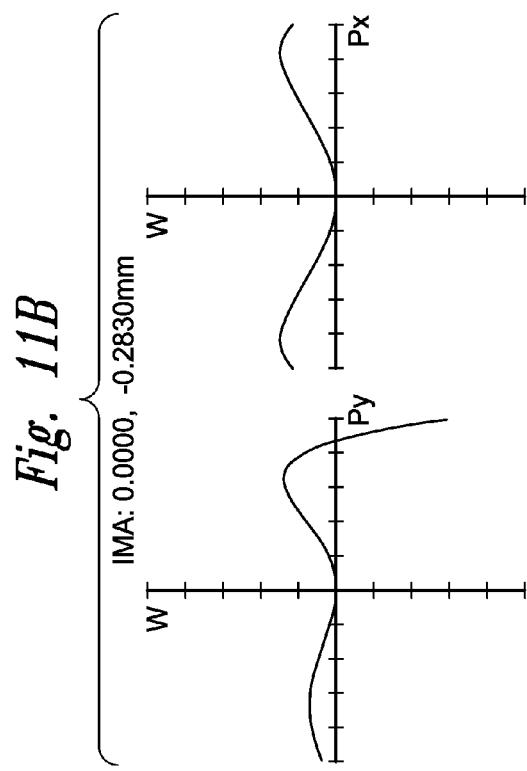

The standard VHIS system consists of two lenses and a highly selective, multiplexed volume hologram. Nominally, these elements are positioned as shown in FIG. 11 (see also FIG. 1), which illustrates an instrument which can observe two axial positions simultaneously by laterally distributing them across the image plane. The system (having coordinates x, y, z) consists of an objective lens 512, a volume hologram 514 placed in the Fourier plane of the objective lens 512, and a collection lens 516. The objective lens 512 receives light from an object 518 disposed in object space (denoted by coordinates x', y', z'), and the collection lens 516 forms a real image 520 of the object in image space (denoted by coordinates x", y", z"). The hologram 514 may comprise a thick hologram having angle-multiplexed planar and spherical wave gratings having high angular and spectral selectivity. A broadband source may be used to illuminate the object. Surface normal axis (→), pupil position (○) and optical axis (dashed line) are shown. This system will produce a projection of the axial position in the object for which the holographic grating is designed. More than one grating may be multiplexed in the hologram, so observation of multiple depths simultaneously is possible. Such a device is useful in observing the 3-dimensional structure of objects, and there is significant interest in using this device to better understand the nature of some cancers. Multiple laboratory prototypes have been built using this conceptual design, mainly in the form of microscopes. As with many optical microscopes, use of the instrument is limited to ex-vivo imaging studies due to the bulk of the instrument.

A Hand-Held VHIS Endoscope is Herein Provided

Figure 12:
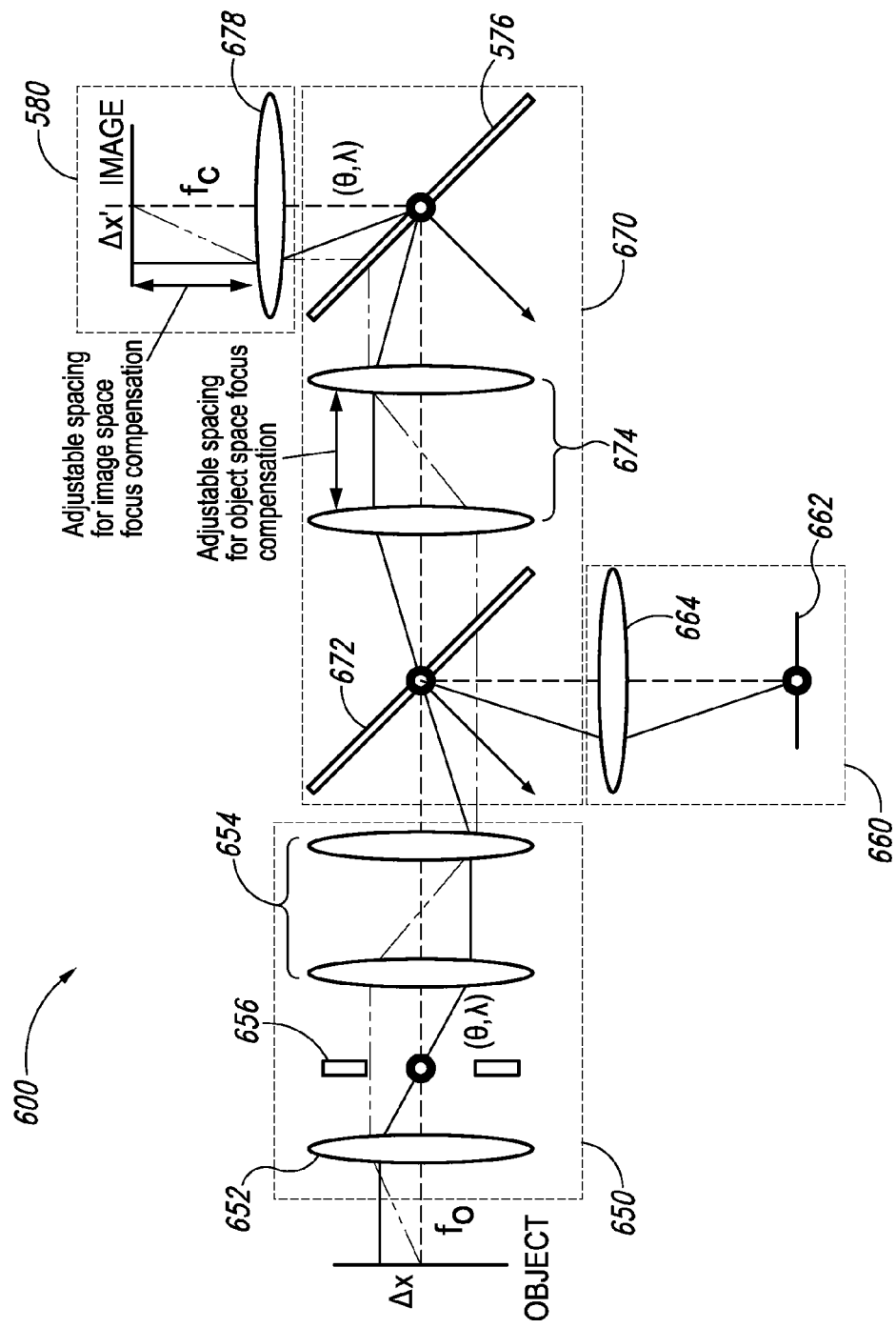
FIG. 12 is an illustration of the structure and operation of one embodiment of a VHIS endoscope having modular components, according to exemplary aspects of the present invention. In this embodiment, the illumination source is designed to be of the Koehler type, which provides broadband illumination at every point across the object field.

The present extension of the ideas of the VHIS to a hand-held microscope are substantially more complex than designing a bench-top microscope and require several design considerations that are illustrated in the layout shown in FIG. 12.

First Exemplary VHIS Endoscope Embodiment

The first consideration in the system design is the layout (FIG. 12). The layout for this instrument, while somewhat similar to the standard VHIS as described herein (FIGS. 1 and 11), has some notable exceptions with respect to: modularity, pupil matching, illumination, and focus compensation. FIG. 12 illustrates the location and functionality of each of the four modular subsystems that make up the exemplary VHIS endoscope device. In this particular device, the illumination source is designed to be of the Koehler type, which provides broadband illumination at every point across the object field. This device will, therefore, not be capable of rejecting energy from out of plane scattering sources, but will provide high resolution projections of each axial position in the object.

Modularity.

Referring to FIG. 12, the modules that make up the exemplary hand-held VHIS endoscopic device 600 are: (1) endoscope attachment (barrel) module 650, (2) illumination module (light source) 660 (Koehler illumination in this exemplary embodiment), (3) handle module 670, (4) imaging module (imaging optics) 680. According to particular aspects, the endoscope attachment (barrel) module 650, the illumination module (light source) 660, and the imaging module (imaging optics) 680 module, are removable from the handle module 670, and may be swapped with compatible respective modules of differing specifications for particular imaging applications. According to additional embodiments, the endoscope attachment (barrel) module 650 is comprised of a (1) a relay module and (2) an objective module.

Miniaturization of the layout is afforded by proper component selection, with the exception of the endoscope attachment module (endoscopic barrel) 650 (which in this embodiment is rigid).

Endoscope Attachment (Barrel) Module 650.

The endoscope attachment module 650 comprises one or a plurality (e.g., a series) of pupil relays 654 with a microscope objective (objective lens) 652 placed at the endoscope's observing end (FIG. 13), the pupil relays 654 configured to preserve an optical wavefront for use with a single or multiplexed volume hologram to select wavefronts originating from different object depths. A system aperture 656 (with pupil position (○)) is positioned between the objective lens 652 and the one or the plurality (series) of pupil relays 654. The specific designs of the endoscope pupil relays 654 and objective 652 are important, and exemplary design layouts are provided herein for reference. The design rules, exception and Zemax design files are discussed below). According to additional embodiments, the endoscope attachment (barrel) module 650 is optionally comprised of a (1) a relay module (e.g., comprising the pupil relays) and (2) an objective module (e.g., comprising the objective lens).

Illumination Options.

The illumination module 660 comprises a light source 662 and a source lens 664. According to particular aspects, there are multiple options available for the illumination module 660 of the inventive endoscope 600 For example, a simple Koehler illumination system that provides broadband illumination to the object may be used to provide for a high-throughput design that allows for the use of relatively inexpensive detectors for image capture. This option, however, does not allow the device to reject light from out-of-plane scattering sources. The final image produced is similar to that of a standard bright field microscope, but with added projections for multiple object planes.

Alternatively, another option for the illumination module 660 is a confocal rainbow system as described in particular embodiments herein. According to particular aspects, a confocal rainbow illumination source allows the device to reject out-of-plane scattering sources, with the disadvantage that the throughput is much lower than when using a Koehler illumination module with the device.

In particular alternate embodiments the illumination module 660 is integral with the handle module 670 to provide an integrated module, and the integrated module is in operative, reversibly attachable communication with the endoscope attachment (barrel) module 650 and the and the imaging module 680.

Handle Module 670.

The handle module 670 comprises a beam splitter 672, a relay 674 having adjustable spacing for object space focus compensation, and hologram 676 (e.g., imaging hologram). The handle module 670 is in operative, reversibly attachable communication with the endoscope attachment (barrel) module 650, the illumination module (light source) 660, and the imaging module 680. In particular alternate embodiments the handle module 670 is integral with the illumination module (light source) 660 and the imaging module 680 to provide an integrated module, and the integrated module is in operative, reversibly attachable communication with the endoscope attachment (barrel) module 650.

Imaging Module 680.

The imaging module 680 comprises a collector lens 678, configured within the imaging module 680 to provide for adjustable spacing for image space compensation. In particular alternate embodiments the imaging module 680 is integral with the handle module 670 to provide an integrated module, and the integrated module is in operative, reversibly attachable communication with the illumination module (light source) 660 and with the endoscope attachment (barrel) module 650.

Also shown in FIG. 12, with respect to the various modules, are: surface normal axis (→); pupil position (○); optical axis (dashed line); chief ray (solid line); marginal ray (dot/dashed line); object height ($\Delta x$); source height ($\Delta x'$); image height ($\Delta x''$), chief ray angle (pupil space) ($\theta$); and chief ray wavelength ($\lambda$).

Second Exemplary VHIS Endoscope Embodiment

Figure 13:
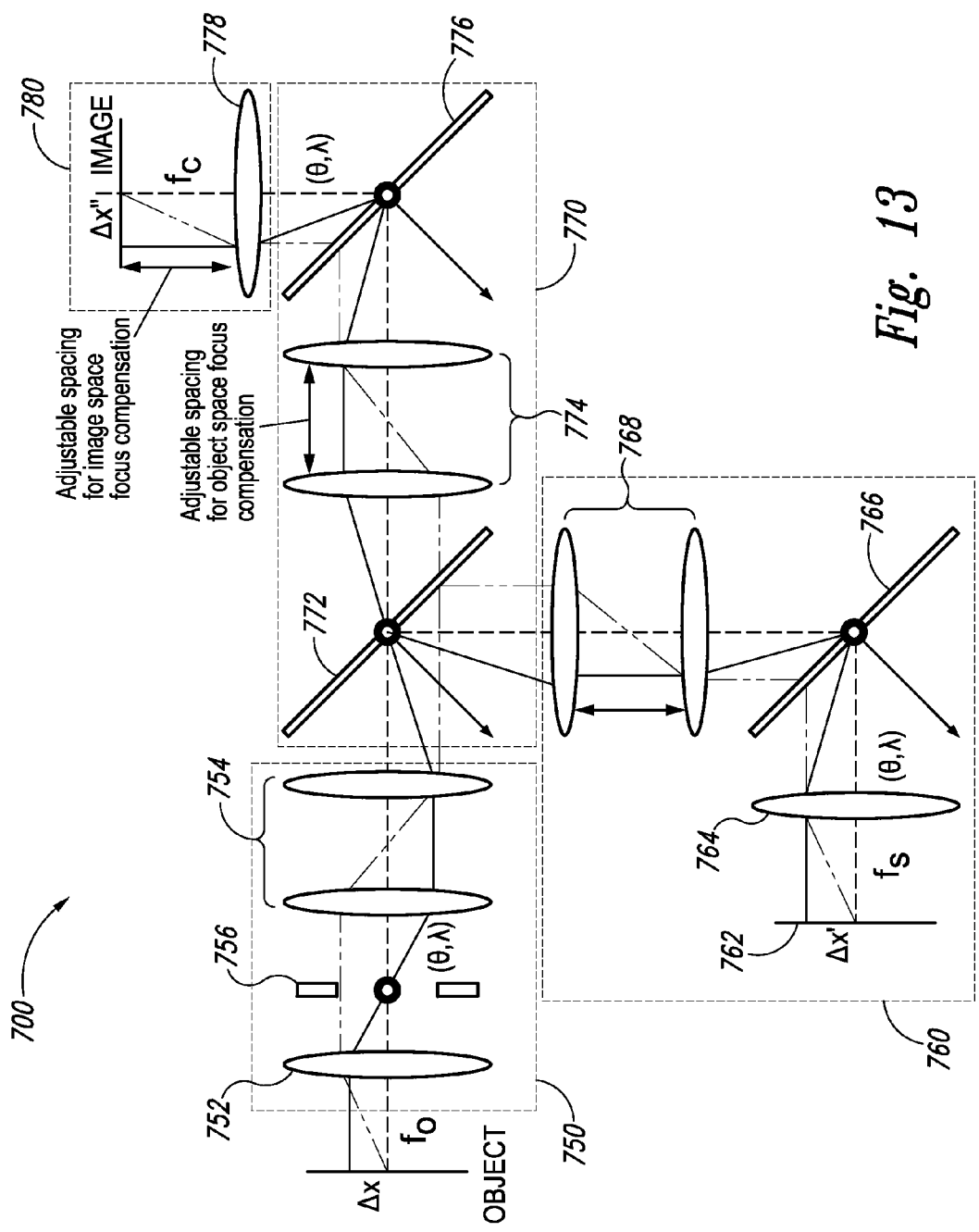
FIG. 13 illustrates the location and functionality of each of the four modular subsystems that make up second exemplary embodiment of the inventive VHIS endoscope device. In this particular device, the illumination source is designed to be of the confocal rainbow system type (as described in detail elsewhere herein), which provides monochromatic illumination at every point across the object field.

FIG. 13 illustrates the location and functionality of each of the four modular subsystems that make up a second exemplary embodiment of the inventive VHIS endoscope device. In this particular device, the illumination source is designed to be of the confocal rainbow system type (as described in detail elsewhere herein), which provides monochromatic illumination at every point across the object field. This particular type of illumination disperses light across the object such that a continuum of colors is projected on the object. This dispersed light is matched angularly to the imaging hologram inside the handle module of the device, which creates an optical sectioning effect, capable of eliminating energy from out-of-plane scattering sources in the object.

Modularity.

Referring to FIG. 13, the modules that make up the second exemplary hand-held VHIS endoscopic device 700 embodiment are: (1) endoscope attachment (barrel) module 750, (2) confocal rainbow illumination module 760, (3) handle module 770, (4) imaging module (imaging optics) 780. According to particular aspects, the endoscope attachment (barrel) module 750, the illumination module (light source) 760, and the imaging module (imaging optics) 780 module, are removable from the handle module 770, and may be swapped with compatible respective modules of differing specifications for particular imaging applications.

As for the first exemplary embodiment, miniaturization of the layout is afforded by proper component selection, with the exception of the endoscope attachment module (endoscopic barrel) 650 (which in this particular embodiment is rigid).

Endoscope Attachment (Barrel) Module 750.

The endoscope attachment module 750 comprises one or a plurality (e.g., a series) of pupil relays 754 with a microscope objective (objective lens) 752 placed at the endoscope's observing end, the pupil relays 754 configured to preserve an optical wavefront for use with a single or multiplexed volume hologram to select wavefronts originating from different object depths. A system aperture (pupil) 756 (with pupil position (○)) is positioned between the objective lens 752 and the one or the plurality (series) of pupil relays 754. The specific designs of the endoscope pupil relays 754 and objective 752 are important, and exemplary design layouts are provided herein for reference. The design rules, exception and Zemax design files are discussed below). According to additional embodiments, the endoscope attachment (barrel) module 750 is optionally comprised of a (1) a relay module (e.g., comprising the pupil relays) and (2) an objective module (e.g., comprising the objective lens).

Illumination Options.

The illumination module 760 comprises a confocal rainbow system as described in particular embodiments herein, a light source 762, a source lens 764, an illumination hologram 766, and a relay 768. The source lens 764 is operatively positioned between the light source 762 and the illumination hologram 766, and the illumination hologram 766 is operatively positioned between the source lens 764 and the a relay 768 (in this embodiment, emitting light at a right angle (normal) to the source optical axis). According to particular aspects, a confocal rainbow illumination source allows the device to reject out-of-plane scattering sources, with the disadvantage that the throughput is relatively lower than when using a Koehler illumination module with the device.

In particular alternate embodiments the illumination module 760 is integral with the handle module 770 to provide an integrated module, and the integrated module is in operative, reversibly attachable communication with the endoscope attachment (barrel) module 750 and the and the imaging module 780.

Handle Module 770.

The handle module 670 comprises a beam splitter 772, a relay 774 having adjustable spacing for object space focus compensation, and hologram 776 (e.g., imaging hologram). The handle module 770 is in operative, reversibly attachable communication with the endoscope attachment (barrel) module 750, the illumination module (light source) 760, and the imaging module 780. In particular alternate embodiments the handle module 770 is integral with the illumination module (light source) 760 and the imaging module 780 to provide an integrated module, and the integrated module is in operative, reversibly attachable communication with the endoscope attachment (barrel) module 750.

Imaging Module 780.

The imaging module 780 comprises a collector lens 778, configured within the imaging module 780 to provide for adjustable spacing for image space compensation. In particular alternate embodiments, the imaging module 780 is integral with the handle module 770 to provide an integrated module, and the integrated module is in operative, reversibly attachable communication with the illumination module (light source) 760 and with the endoscope attachment (barrel) module 750.

Also shown in FIG. 13, with respect to the various modules, are: surface normal axis (→); pupil position (○); optical axis (dashed line); chief ray (solid line); marginal ray (dot/dashed line); object height ($\Delta x$); source height ($\Delta x'$), image height ($\Delta x''$), chief ray angle (pupil space) ($\theta$); and chief ray wavelength ($\lambda$).

Exemplary Endoscope Attachment (Barrel) Module Embodiment

Figure 14:
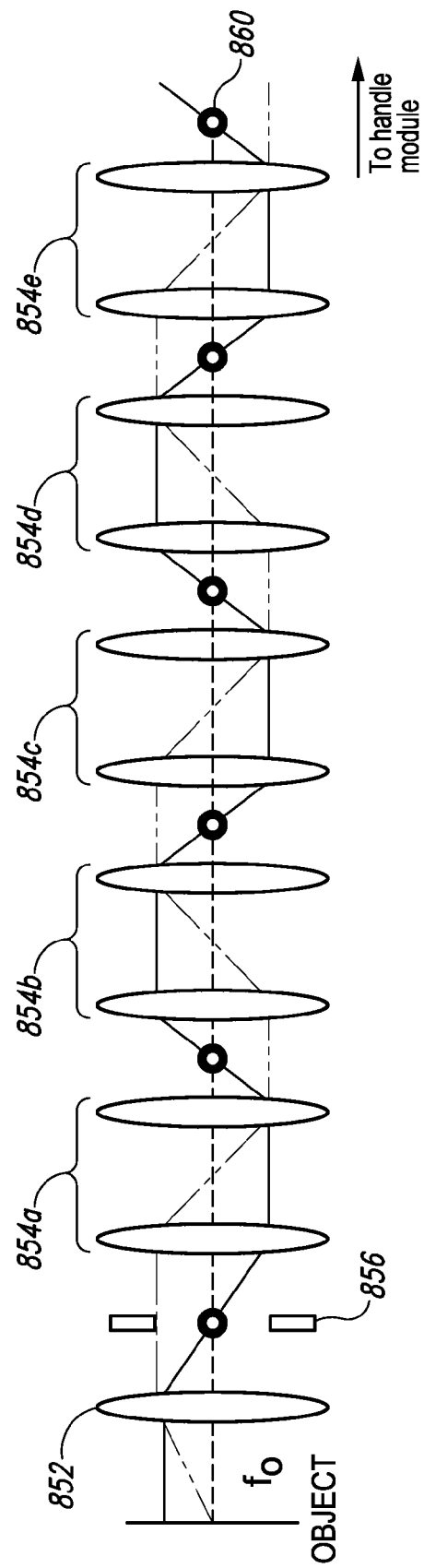
FIG. 14 illustrates a schematic of an exemplary endoscope barrel according to aspects of the present invention. This design uses 5 relay stages to produce an image of the system aperture at the output of the barrel.

FIG. 14 illustrates an endoscope attachment (barrel) module 850 embodiment according to particular aspects of the invention. The exemplary endoscope attachment module 850 comprises 5 relay stages (854a through 854e) to produce an image of the system aperture at the output (e.g., exit pupil) 860 of the barrel. The first relay stage 854a is specifically designed and configured to compensate the off-axis aberrations of an aspheric singlet microscope objective 852. The other 4 relay stages (854b through 854e) are corrected for infinite conjugates and are designed and configured to be modular (these are the modular relay stages). Note that these relays are propagating a planar wavefront through the system, as the wavefront is nominally planar in the pupil (system aperture) 856 of the system. Also shown in FIG. 14, are: pupil positions ($\theta$); optical axis (dashed line); chief ray (solid line); and marginal ray (dot/dashed line).

Exemplary Modular Pupil Relay Embodiment

FIGS. 15A and B illustrate an exemplary design configuration of a modular pupil relay (954b) (as suitable for use in the above-described endoscope attachment (barrel) module 850 embodiment), which is designed for infinite conjugates, and employs a Hopkins rod 982 in the middle to extend the length of the design. It is designed to be monochromatic at each field angle, though the wavelength changes linearly (approximately) with angle over the field. Field curvature is removed as an aberration by slightly curving the object plane, as this is an acceptable compromise for the application. Correction of the monochromatic aberrations is achieved, for example, by using simple glass shapes (bi-convex, planoconvex, and plano-concave) and by employing basic rules of $3^{rd}$ order optical aberration theory. The first 970 and last 980 bi-convex lenses largely determine the spherical aberration of the system, and adjusting their radii is the primary means by which this aberration is tuned. The inner plano-convex lenses 972 and 978 determine the system's astigmatism, and adjusting their radii tunes this aberration. The negative plano-concave elements 974 and 976 introduce negative spherical aberration and astigmatism, which balances with the positive elements in the system. They also reduce the overall field curvature component of the Seidel sum. Since all of the glass shapes are simple, these lenses are commercially available in catalogs. FIG. 15 B shows Optical path difference plots for the modular pupil relay (954b) of FIG. 15A.

Exemplary Microscope Objective and Compensating Pupil Relay Embodiment

Figure 16A:
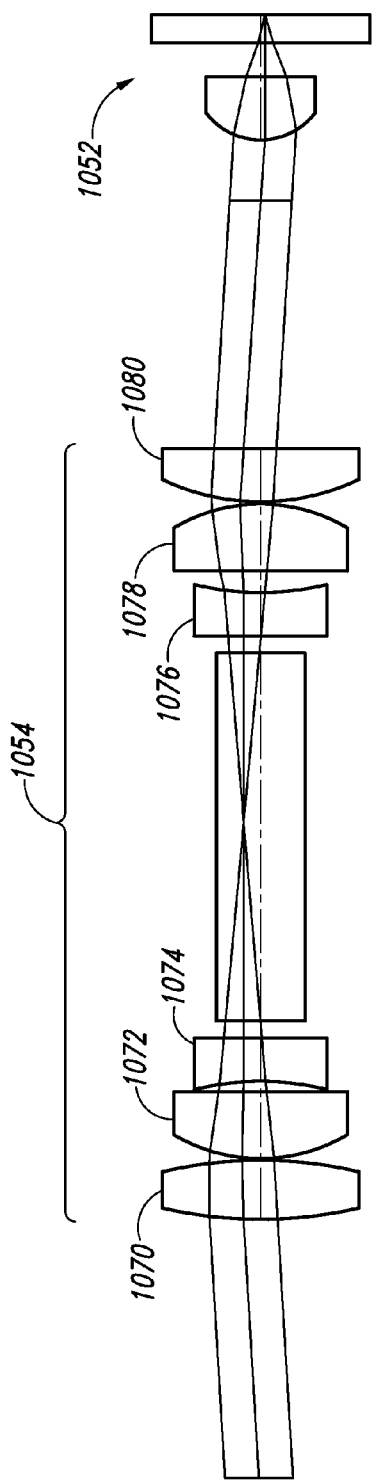
FIGS. 16A and B illustrate an exemplary design configuration of a microscope objective and compensating pupil relay embodiment (as suitable for use in the endoscope attachment (barrel) module of FIG. 14).
Figure 16B:
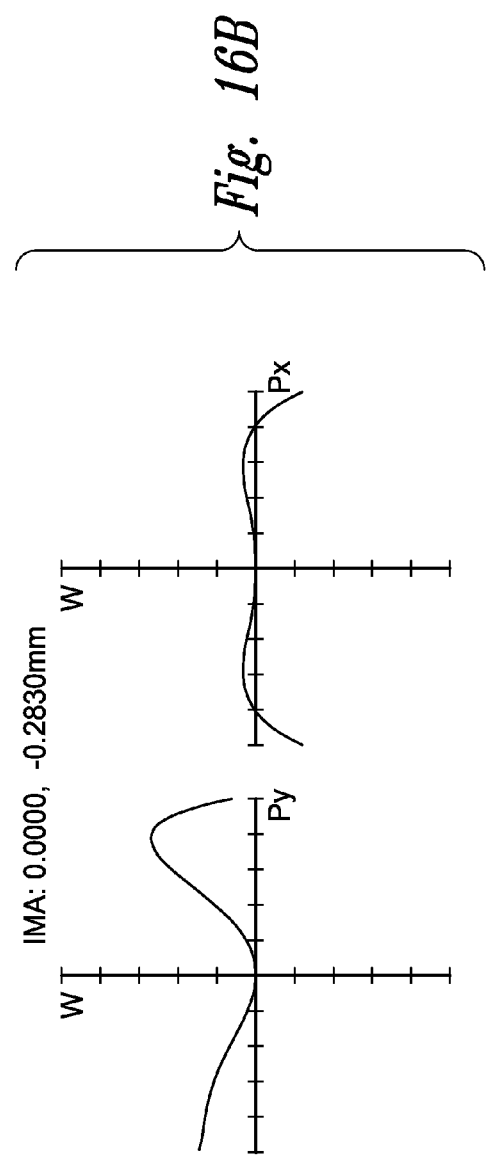

FIGS. 16A and B illustrate an exemplary design configuration of a microscope objective (1052) and compensating pupil relay embodiment (1054) (as suitable for use in the above-described endoscope attachment (barrel) module 850 embodiment). This part of the endoscope is designed for infinite conjugates, and uses a commercial diode-collimating asphere 1052 as a microscope objective lens. Since this asphere is well corrected on-axis, it can be used at a large numerical aperture (~0.4) to obtain high resolution images. The field of the objective is corrected in the compensating pupil relay 1054. Since the system is monochromatic at each field point, only astigmatism and coma need to be considered in the aberration analysis. The astigmatism is corrected by equally adjusting the radii of the inner plano-convex elements 1074 and 1076. The coma is largely corrected by the asymmetry of the first 1080 and last 1070 elements of the relay, and it is tuned by adjusting the air space between the second plano-concave lens 1078 and the subsequent plano-convex lens 1076. Since all of the elements have simple shapes (piano-convex, bi-convex, plano-concave), they are cheap, and readily found in commercial catalogs. FIG. 16 B shows Optical path difference plots for the compensating pupil relay (1054) of FIG. 15A.

Figure 17A:
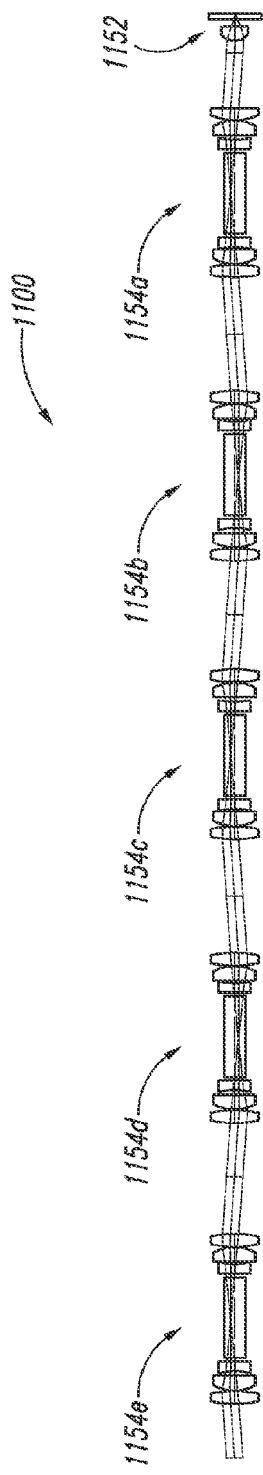
FIGS. 17A-C illustrate an exemplary complete endoscope probe design (as suitable for use in the endoscope attachment (barrel) module of FIG. 14).
Figure 17B:
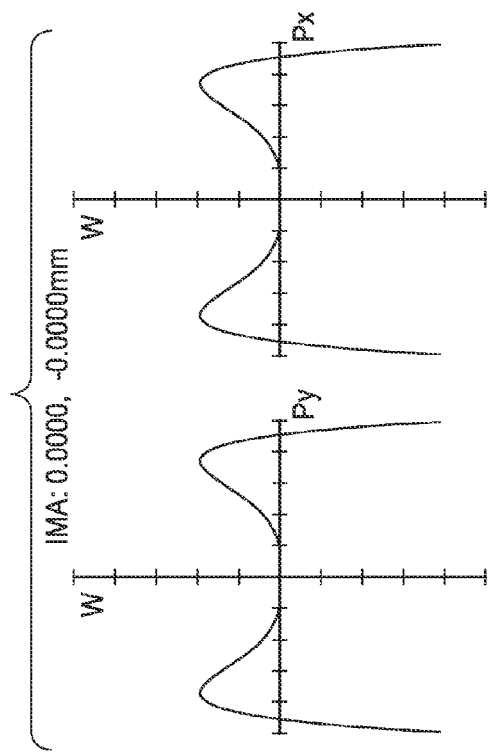
Figure 17C:
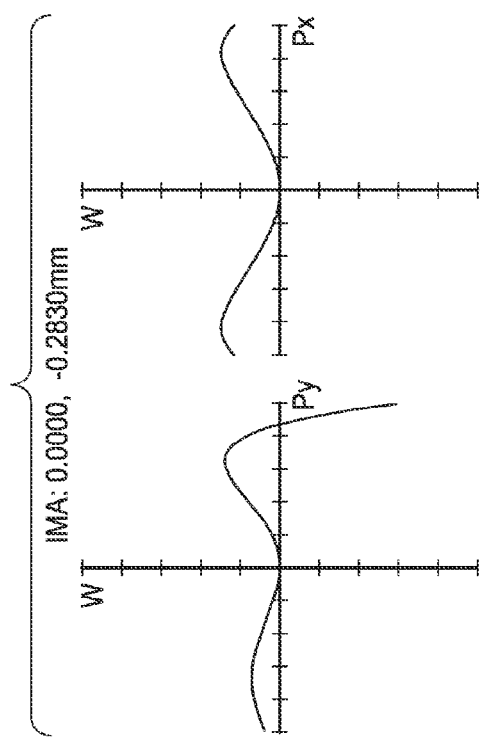

Exemplary Endoscopic Probe (Endoscope Attachment (Barrel) Module) Embodiment FIGS. 17A-C illustrate an exemplary complete endoscope probe design (as suitable for use in the above-described endoscope attachment (barrel) module 850 embodiment). Shown are microscope objective (1152) (e.g., a commercial diode-collimating asphere as a microscope objective lens), compensating pupil relay system (1154a), and a modular pupil relay (1154b through 1154e) (all as suitable for use in the above-described endoscope attachment (barrel) module 850 embodiment). Bi-convex, planoconvex, and plano-concave glass shapes are shown for the elements, and are configured as described above in relation to the modular pupil relay embodiments, and the microscope objective and compensating pupil relay embodiments.

The optical path difference (OPD) plots (FIGS. 17B and C) show that the design is well corrected over the field, with essentially diffraction-limited performance. The field is slightly curved inward to accommodate field curvature, and it is also slightly tilted to allow a focal plane shift across the field. The departure from a plane for a 566×566 urn field of view is ~28 urn at the edge. This has been deemed acceptable for the observation of biological specimens.

Figure 18:
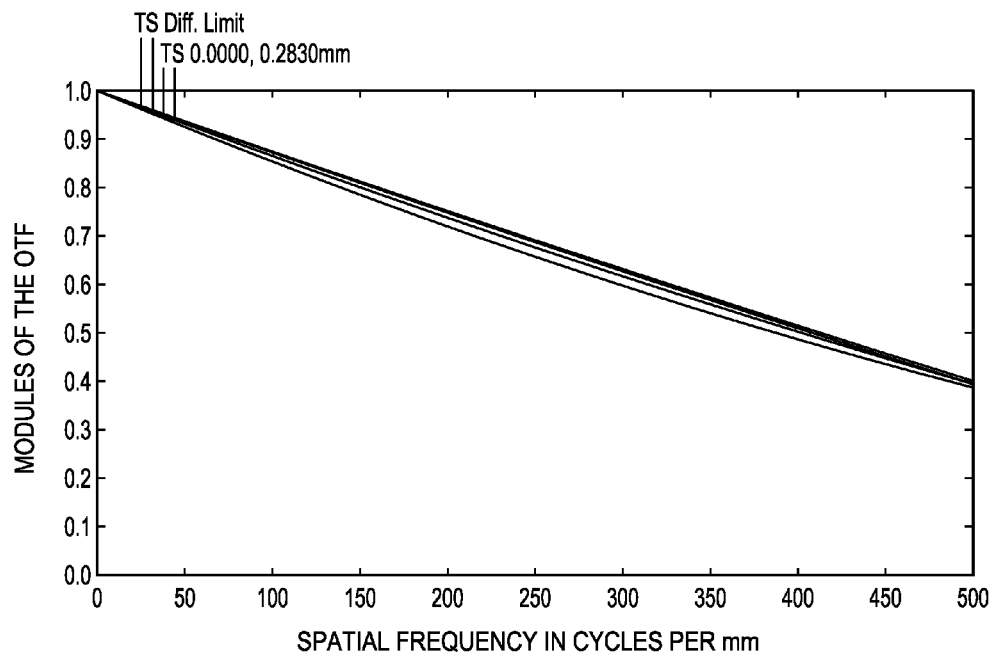
FIG. 18 illustrates an exemplary VHIS endoscope layout, single grating confocal embodiment.

FIG. 18 shows an estimated performance curve an endoscope barrel according to particular aspects of the invention as disclosed and discussed in the above-described exemplary embodiments. This is a simulation of the optical contrast curve at the edge of the field.

Figure 19:
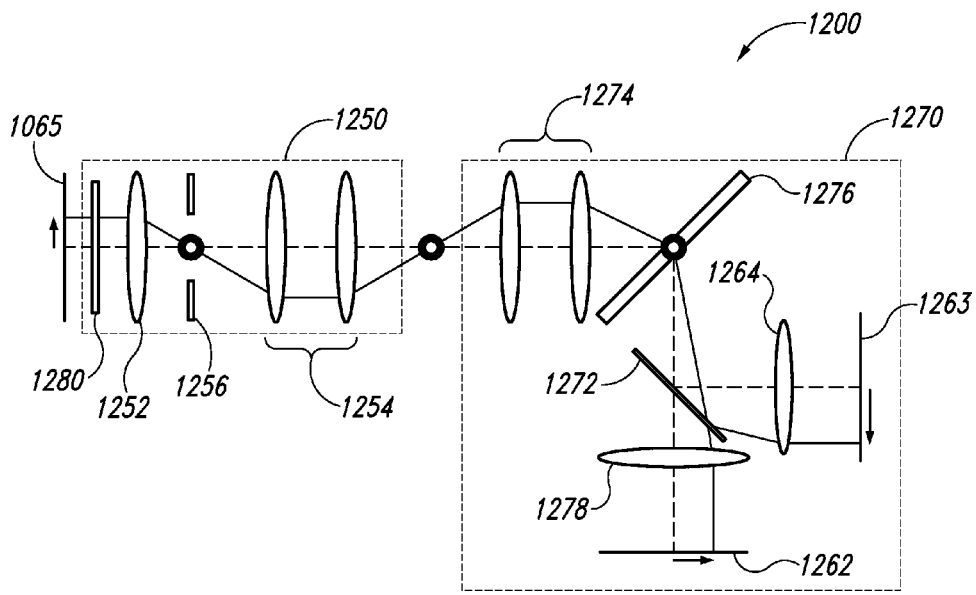
FIG. 19 illustrates an exemplary VHIS endoscope layout, single grating confocal embodiment. This version of the VHIS endoscope uses a common-path broadband light source and source lens to provide illumination at the object plane

Additional Exemplary VHIS Endoscope Layout, Single Grating Confocal Embodiment FIG. 19 illustrates an exemplary VHIS endoscope layout, single grating confocal embodiment 1200. This version of the VHIS endoscope uses a common-path broadband light source 1262 and source lens 1264 to provide illumination at the object plane. The source 1262 position is chosen such that the source 1263 and object planes 1265 are confocal. The hologram 1276 disperses the light from the source plane 1063 such that each point along the dispersive axis of the object plane 1065 is essentially monochromatically illuminated, creating an optical sectioning effect with a characteristic optical section thickness.

In this embodiment, the endoscope attachment (barrel) module 1250 comprises one or a plurality (e.g., a series) of pupil relays 1254 with a microscope objective (objective lens) 1252 placed at the endoscope's observing end, the pupil relays 754 configured to preserve an optical wavefront for use with a single or multiplexed volume hologram to select wavefronts originating from different object depths. A system aperture (pupil) 1256 (with pupil position (○)) is positioned between the objective lens 1252 and the one or the plurality (series) of pupil relays 1254. A window 1280 is also shown.

In this embodiment the common-path broadband light source 1262 and source lens 1264, as well as the collector lens 1278 are integral to the endoscopic handle module 1270, along with beam splitter 1272, hologram 1276, and relay 1274 (which is configured for variable spacing for focus compensation). Alternatively, these source and collection elements could be reversibly coupled to less complex endoscopic handle module, in the context of separate modules in the spirit of the present invention, and as illustrated above in the other exemplary embodiments.

Exemplary Flexible VHIS Endoscope Embodiment Having the VHIS Packaged at the Distal Tip According to additional aspects of the invention, one or more of the four modules (as discussed in detail herein) that make up the VHIS endoscopic device, or elements of these modules, are packaged in a flexible tip system. According to particular aspects, and with reference to FIG. 29, at least the objective lens 2004, hologram 2006 and collector lens 2008 are configured in a flexible tip system 2000 of a VHIS endoscopic device. In particular aspects flexible cable, in operative communication with the flexible tip system 2000, is used to carry at least one of electrical signals from the camera 2010 and optical fiber for illumination of the tissue sample.

Figure 29:
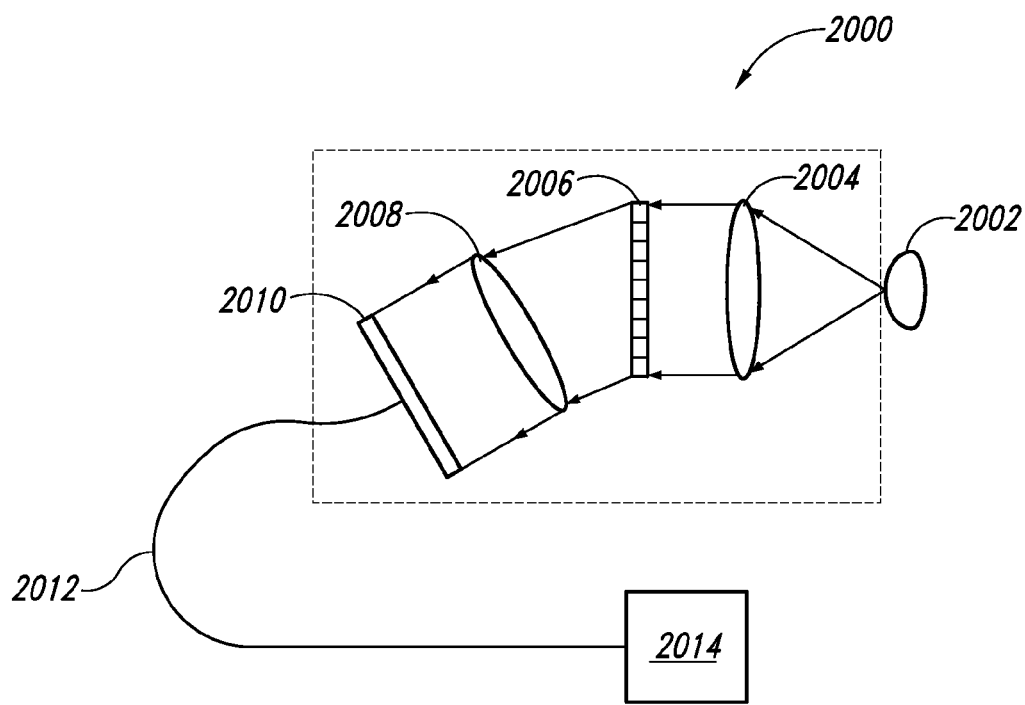
FIG. 29 illustrates an exemplary flexible endoscope embodiment with the VHIS packaged at a distal tip system.

FIG. 29 illustrates an exemplary flexible endoscope embodiment with the VHIS packaged at a distal tip system 2000, being place proximate to a tissue 2002. Shown are objective lens 2004; hologram 2006; collector lens 2008, camera 2010; flexible cable 2012 and monitor 2014. The flexible cable 2012 can carry both electrical signals from the camera 2010 and optical fiber for illumination of the tissue sample.

According to particular aspects, while rigid VHIS endoscopic instruments can be effectively used in minimally invasive clinical procedures, the disclosed more flexible VHIS endoscopic embodiments provide even more clinical utility, wherein more precise or articulated surgical movements are necessary.

Optical Design for the Volume Holographic Imaging System (VHIS) Endoscope

The following discussion summarizes conceptual design rules employed by Applicants in providing the VHIS endoscope embodiments disclosed and discussed herein.

VHIS Endoscope Design Rules.

General concepts according to particular aspects of the present invention:

A modular design was conceived as optimal for design scalability and adaptability; namely enabling endoscope length and field changes depending upon the application;

In certain aspects, two types of modules are required for creating a rigid endoscope (barrel; attachment) module as described herein; (1) a relay module and (2) an objective module. The relay module provides the required length for the endoscope, and the objective module defines the imaging characteristics; and The modules are designed to be easily connected and interchangeable.

Module design requirements and exceptions are as follows:

The nominal wavefront in the entrance pupil is planar and has a specified angular bandwidth;

The nominal wavefront in the exit pupil is corrected to be within the diffraction limit or better;

For a VHIS system, axial chromatic aberration may be excluded from analysis because each field point is monochromatic. Focus shift across the field of view is compensated by slightly tilting the object plane;

Field curvature may be excluded from analysis because the object plane can be curved a small amount to compensate this aberration VHIS Endoscope Relay Module Design Rules.

General concepts according to particular aspects of the present invention:

A repeated optical unit is required for the propagation of a pupil down a single axis; and Such a repetition must have an angular acceptance range and entrance pupil diameter compatible with microscope objectives.

Design requirements and exceptions are as follows:

The nominal wavefront in the entrance pupil is planar and has a specified angular bandwidth;

The nominal wavefront in the exit pupil is corrected to be planar within the diffraction limit or better;

For a VHIS system, axial chromatic aberration may be excluded from analysis because each field point is monochromatic. Focus shift across the field of view is compensated by slightly tilting the object plane;

Field curvature may be excluded from analysis because the object plane can be curved a small amount to compensate this aberration; and Unit magnification is 1:1.

Design Method aspects according to aspects of the invention:

Cancel all odd aberrations using symmetry (Coma, Distortion, Lateral Color are all zero);

Designate 2 surfaces for the independent correction of spherical aberration and astigmatism;

Correct field curvature by having positive and negative lenses;

Extend the physical distance of the unit by introducing a Hopkins rod lens of zero power;

Use all the same glass type (N-BK7) for availability of components; and

All elements are of a simple shape type (piano-convex, plano-concave, bi-convex) for ease of manufacturing.

Figure 20:
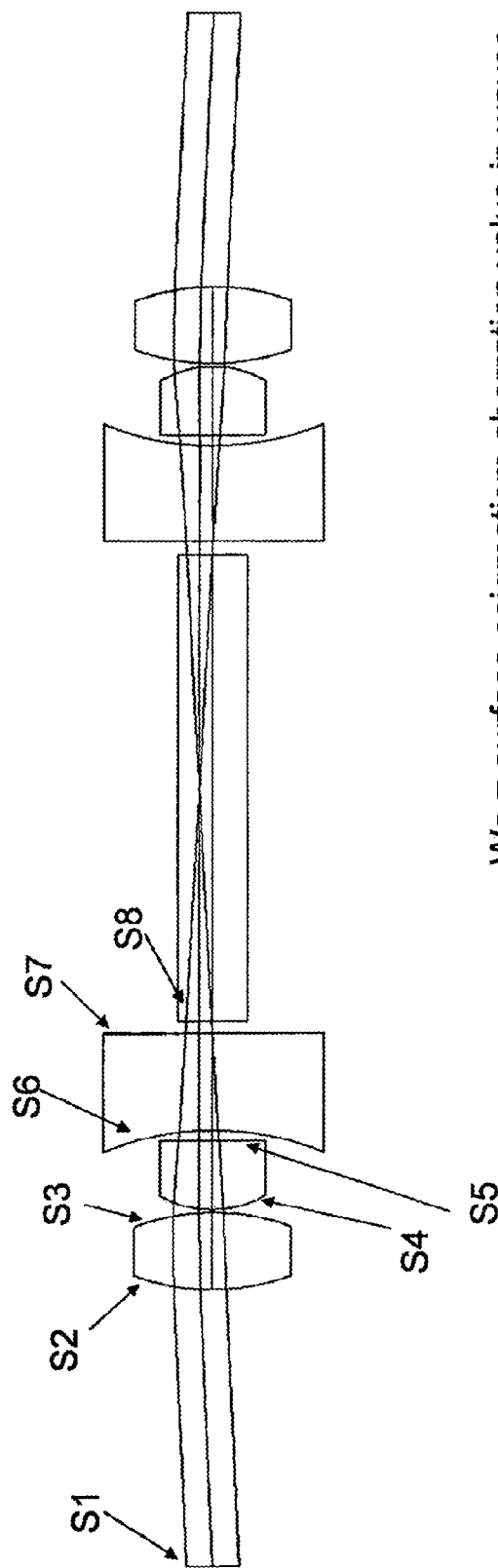
FIG. 20 shows an exemplary design configuration of a modular pupil relay showing various surfaces (S1 through S8) present on the bi-convex, planoconvex, and planoconcave elements of the pupil relay (as suitable for use in the endoscope attachment (barrel) modules disclosed herein).

FIG. 20 shows an exemplary design configuration of a modular pupil relay showing various surfaces (S1 through S8) present on the bi-convex, planoconvex, and plano-concave elements of the pupil relay (as suitable for use in the endoscope attachment (barrel) modules disclosed herein), in keeping with the above described rules, exceptions.

Figure 21:
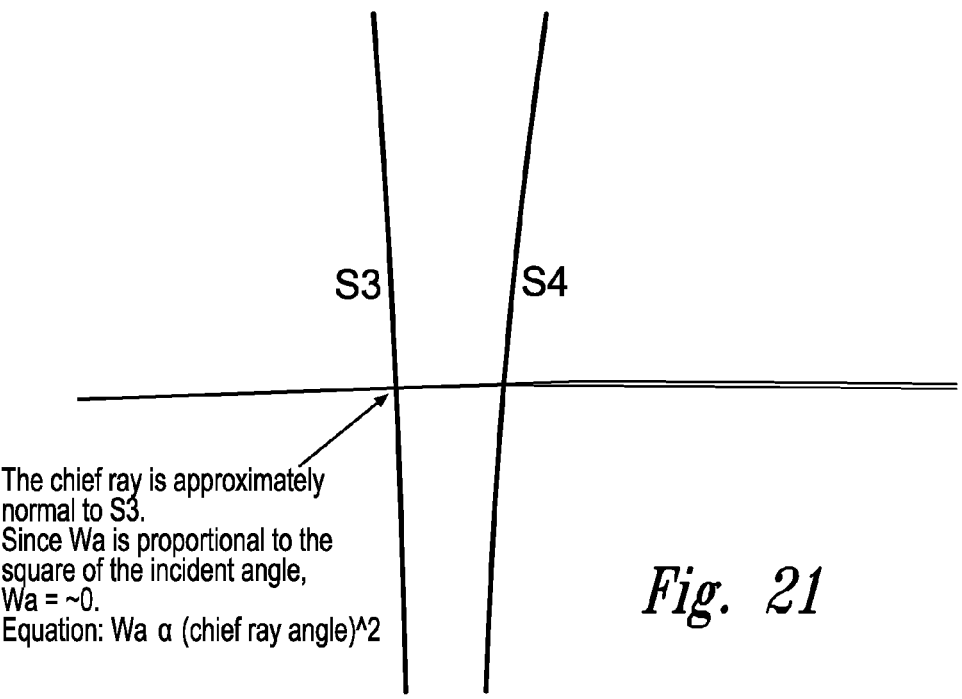
FIG. 21 shows, with respect to the design configuration and various surfaces (S1 through S8) of FIG. 20, that when the chief ray is approximately normal to S3, since Wa (i.e., surface astigmatism aberration value in waves) is proportional to the square of the incident angle, Wa=~0.

FIG. 21 shows, with respect to the design configuration and various surfaces (S1 through S8) of FIG. 20, that when the chief ray is approximately normal to S3, since Wa (i.e., surface astigmatism aberration value in waves) is proportional to the square of the incident angle, Wa=~0.

Figure 22:
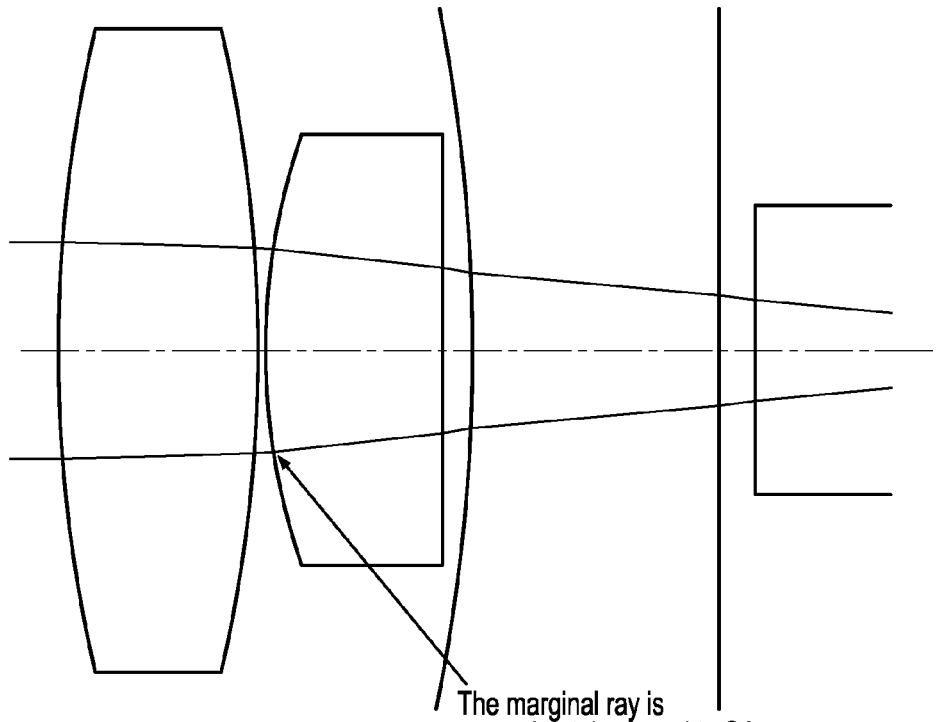
FIG. 22 shows, with respect to the design configuration and various surfaces (S1 through S8) of FIG. 20, that when the marginal ray is approximately normal to S4, since Ws (i.e., surface spherical aberration value in waves) is proportional to the marginal ray angle squared, Ws=~0.

FIG. 22 shows, with respect to the design configuration and various surfaces (S1 through S8) of FIG. 20, that when the marginal ray is approximately normal to S4, since Ws (i.e., surface spherical aberration value in waves) is proportional to the marginal ray angle squared, Ws=~0.

Tables 1 and 2 below show representative Seidel Coefficients; Seidel Aberration Coefficients in Waves (Table 1), along with Lens Data Editor configuration parameters (Table 2).

TABLE 1

Seidel Coefficients
Seidel Aberration Coefficients in Waves:

| Surf | W040 | W131 | W222 | W220P | W311 | W020 | W111 |
|---|---|---|---|---|---|---|---|
| STO | −0.000000 | 0.000000 | −0.000000 | −0.000000 | 0.000000 | −0.000000 | 0.000000 STO |
| 2 | 0.029667 | −0.164305 | 0.227492 | 0.076986 | −0.528165 | −0.000000 | 0.000000 BCX1, Thor LB1212 |
| 3 | 0.379596 | −0.081665 | 0.004392 | 0.076986 | −0.008518 | 0.000000 | −0.000000 BCX1, Thor LB1212 |
| 4 | −0.014064 | 0.078691 | −0.110075 | 0.175844 | −0.337973 | −0.000000 | 0.000000 PCX1, CVI LPX-6.0-8.8-C |
| 5 | 0.555541 | −0.211174 | 0.020068 | −0.000000 | −0.001907 | 0.000000 | −0.000000 PCX1, CVI LPX-6.0-8.8-C |
| 6 | −0.935449 | 0.827112 | −0.182831 | −0.060211 | 0.067033 | 0.000000 | −0.000000 PCV1, Thor LC1439 |
| 7 | 0.238855 | 0.000853 | 0.000001 | 0.000000 | 0.000000 | 0.000000 | 0.000000 PCV1, Thor LC1439 |
| 8 | −0.239520 | −0.000856 | −0.000001 | −0.000000 | −0.000000 | 0.000000 | 0.000000 glass rod |
| 9 | −0.241055 | −0.000861 | −0.000001 | −0.000000 | −0.000000 | −0.000000 | −0.000000 glass rod |

TABLE 1-continued

Seidel Coefficients
Seidel Aberration Coefficients in Waves:

| Surf | W040 | W131 | W222 | W220P | W311 | W020 | W111 | |
|---|---|---|---|---|---|---|---|---|
| 10 | 0.240257 | 0.000858 | 0.000001 | 0.000000 | 0.000000 | −0.000000 | −0.000000 | PCV2, Thor LC1439 |
| 11 | −0.942759 | −0.839189 | −0.186749 | −0.060211 | −0.068357 | −0.000000 | −0.000000 | PCV2, Thor LC1439 |
| 12 | 0.558726 | 0.216252 | 0.020925 | −0.000000 | 0.002025 | −0.000000 | −0.000000 | PCX2, CVI LPX-6.0-8.8-C |
| 13 | −0.013830 | −0.076831 | −0.106707 | 0.175844 | 0.340240 | 0.000000 | 0.000000 | PCX2, CVI LPX-6.0-8.8-C |
| 14 | 0.380764 | 0.084609 | 0.004700 | 0.076986 | 0.008815 | −0.000000 | −0.000000 | BCX2, Thor LB1212 |
| 15 | 0.030761 | 0.169166 | 0.232577 | 0.076986 | 0.531443 | 0.000000 | 0.000000 | BCX2, Thor LB1212 |
| 16 | 0.000000 | 0.000000 | 0.000000 | −0.000000 | −0.000000 | 0.000000 | 0.000000 | |
| 17 | 0.000000 | 0.000000 | 0.000000 | 0.000000 | 0.000000 | 0.000000 | 0.000000 | |
| 18 | −0.000000 | −0.000000 | −0.000000 | −0.000000 | −0.000000 | −0.000000 | −0.000000 | |
| 19 | −0.000000 | −0.000000 | −0.000000 | −0.000000 | −0.000000 | −0.000000 | −0.000000 | |
| IMA | 0.000000 | 0.000000 | 0.000000 | 0.000000 | 0.000000 | 0.000000 | 0.000000 | |
| TOT | 0.027489 | 0.002662 | −0.076208 | 0.539210 | 0.004637 | 0.000000 | 0.000000 | |

TABLE 2

Lens Data Editor: Config 1/3

| Surf: Type | Comment | Radius | Thickness | | Glass | |
|---|---|---|---|---|---|---|
| OBJ Standard | | Infinity | Infinity | | | |
| STO Standard | STO | Infinity | 9.989 | V | | |
| 2* Standard | BCX1, Thor LB1 . . . | 20.100 | 2.800 | | N-BK7 | |
| 3* Standard | BCX1, Thor LB . . . | −20.100 | 0.100 | | | |
| 4* Standard | PCX1, CVI LPX . . . | 8.800 | 2.500 | | N-BK7 | |
| 5* Standard | PCX1, CVI LPX . . . | Infinity | 0.400 | | | |
| 6* Standard | PCV1, Thor LC . . . | −25.700 | 3.500 | | N-BK7 | |
| 7* Standard | PCV1, Thor LC . . . | Infinity | 0.480 | V | | |
| 8* Standard | glass rod | Infinity | 17.000 | | F2 | |
| 9* Standard | glass rod | Infinity | 0.480 | P | | |
| 10* Standard | PCV2, Thor LC . . . | Infinity P | 3.500 | P | N-BK7 | P |
| 11* Standard | PCV2, Thor LC . . . | 25.700 P | 0.400 | P | | |
| 12* Standard | PCX2, CVI LPX . . . | Infinity P | 2.500 | P | N-BK7 | P |
| 13* Standard | PCX2, CVI LPX . . . | −8.800 P | 0.100 | P | | |
| 14* Standard | BCX2, Thor LB . . . | 20.100 P | 2.800 | P | N-BK7 | P |
| 15* Standard | BCX2, Thor LB . . . | −20.100 P | 10.028 | C | | |
| 16 Standard | | Infinity | 4.100 | | | |
| 17* Paraxial | | | 4.100 | | | |
| 18 Standard | | Infinity | 0.00 | | | |
| 19 Coordinat . . . | | | 0.000 | | — | |
| IMA Standard | | −9.783 | V | | — | |

Figure 23:
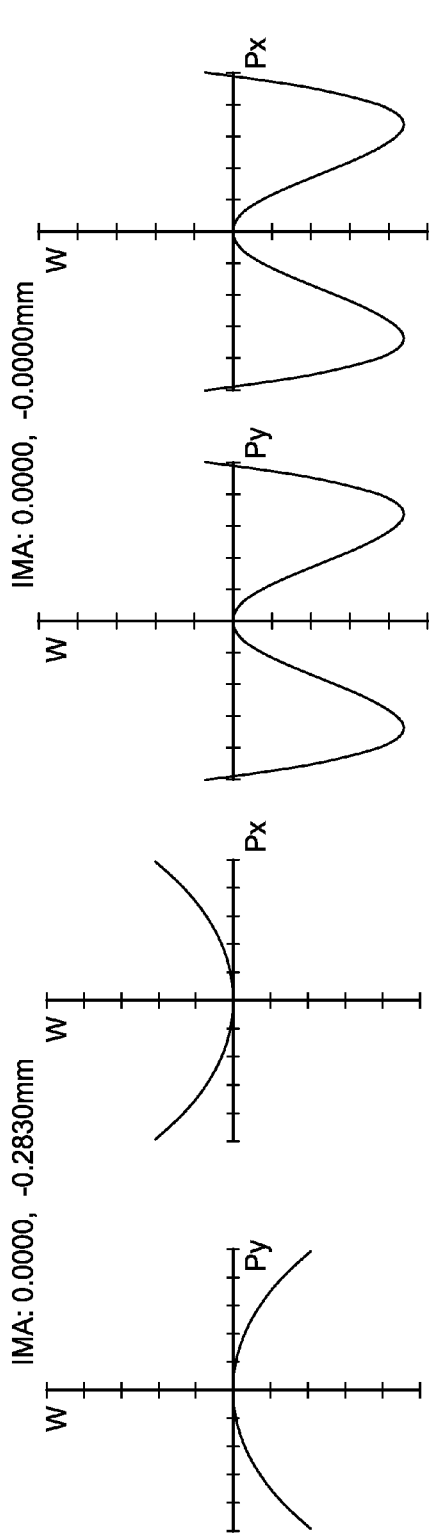
FIG. 23 shows representative optical path difference plots, with respect to the design configuration and various surfaces (S1 through S8) of FIG. 20, and parameter of Tables 1 and 2.

FIG. 23 shows representative optical path difference plots, with respect to the design configuration and various surfaces (S1 through S8) of FIG. 20, and parameter of Tables 1 and 2.

Extending the Design to a Generalized Endoscope Relay Module Design Improvements According to Aspects of the Invention:

Correction of axial color can be achieved by changing the glass type of the negative element•(change to a flint element with Abbe# less than 35). The radius of S6 must be changed to maintain correction of the Ws and Wa totals. The glass type of the biconvex element may also be changed to a less dispersive type to improve chromatic performance; and Keeping the airspace small (<0.2 mm) between the negative element and the glass rod can keep S7 and S8 from contributing to the wavefront aberration total.

Figure 24:
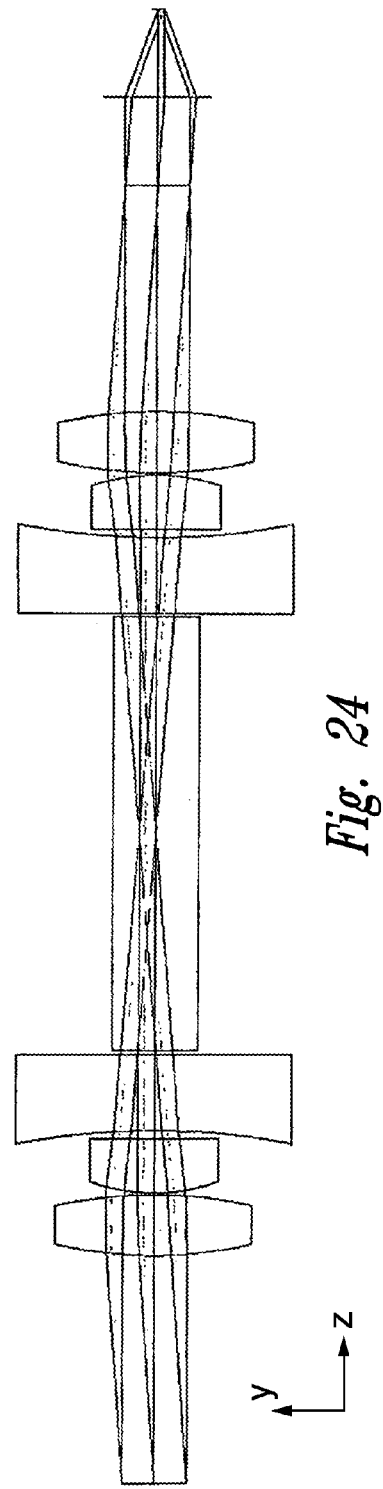
FIG. 24 shows an exemplary 3D layout of a pupil relay according to the present invention, and showing Hopkins rod, and plano-convex, plano-concave, bi-convex glass elements as discussed in detail herein above.

FIG. 24 shows an exemplary 3D layout of a pupil relay according to the present invention, and showing Hopkins rod, and plano-convex, plano-concave, bi-convex glass elements as discussed in detail herein above.

Figure 25:
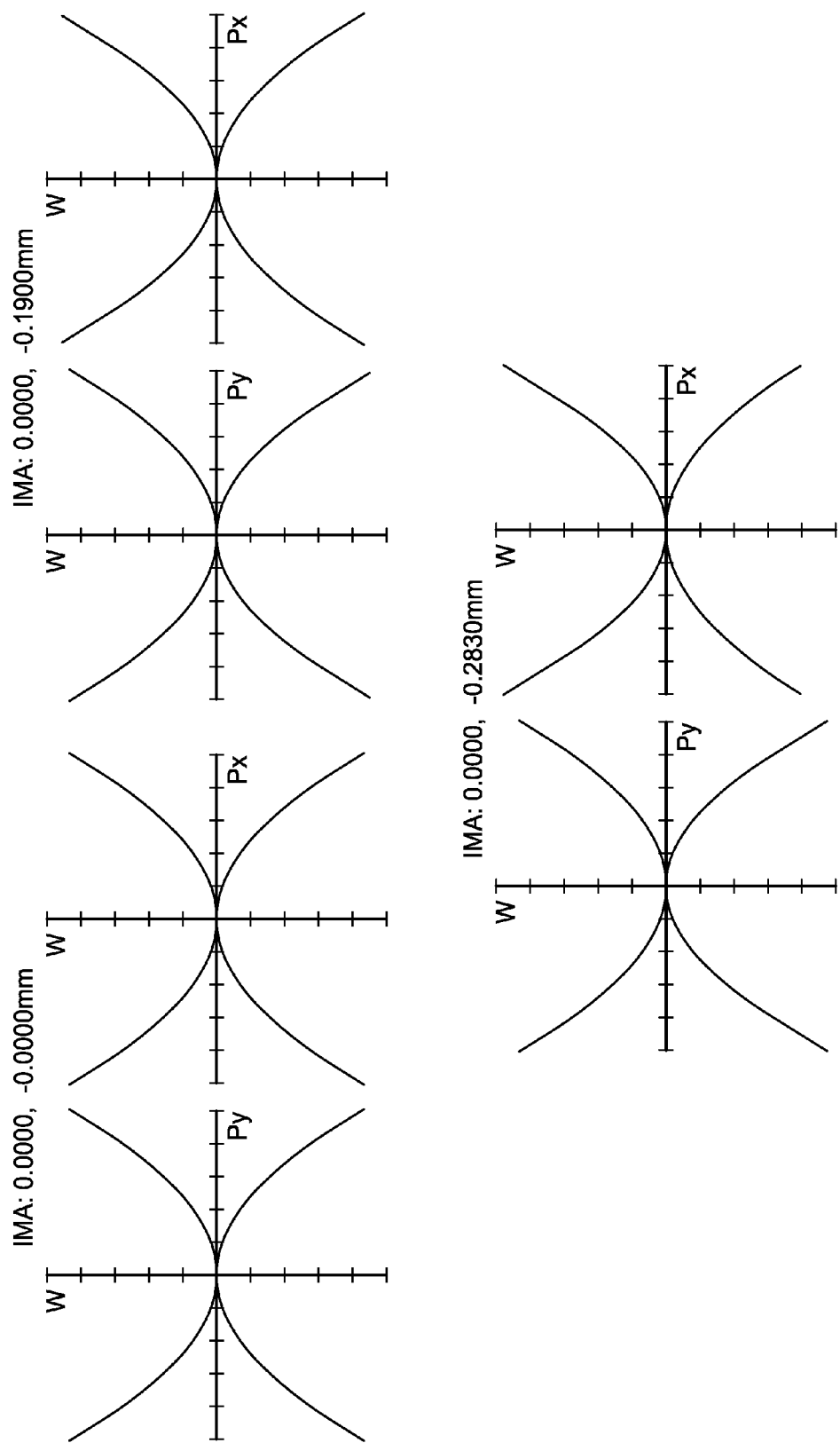
FIGS. 25 and 26 show, with respect to 3D layout of a pupil relay of FIG. 24, relay performance for a 80 nm bandwidth in the form of Optical Path Difference plots, before and after, respectively, changing glass types
Figure 26:
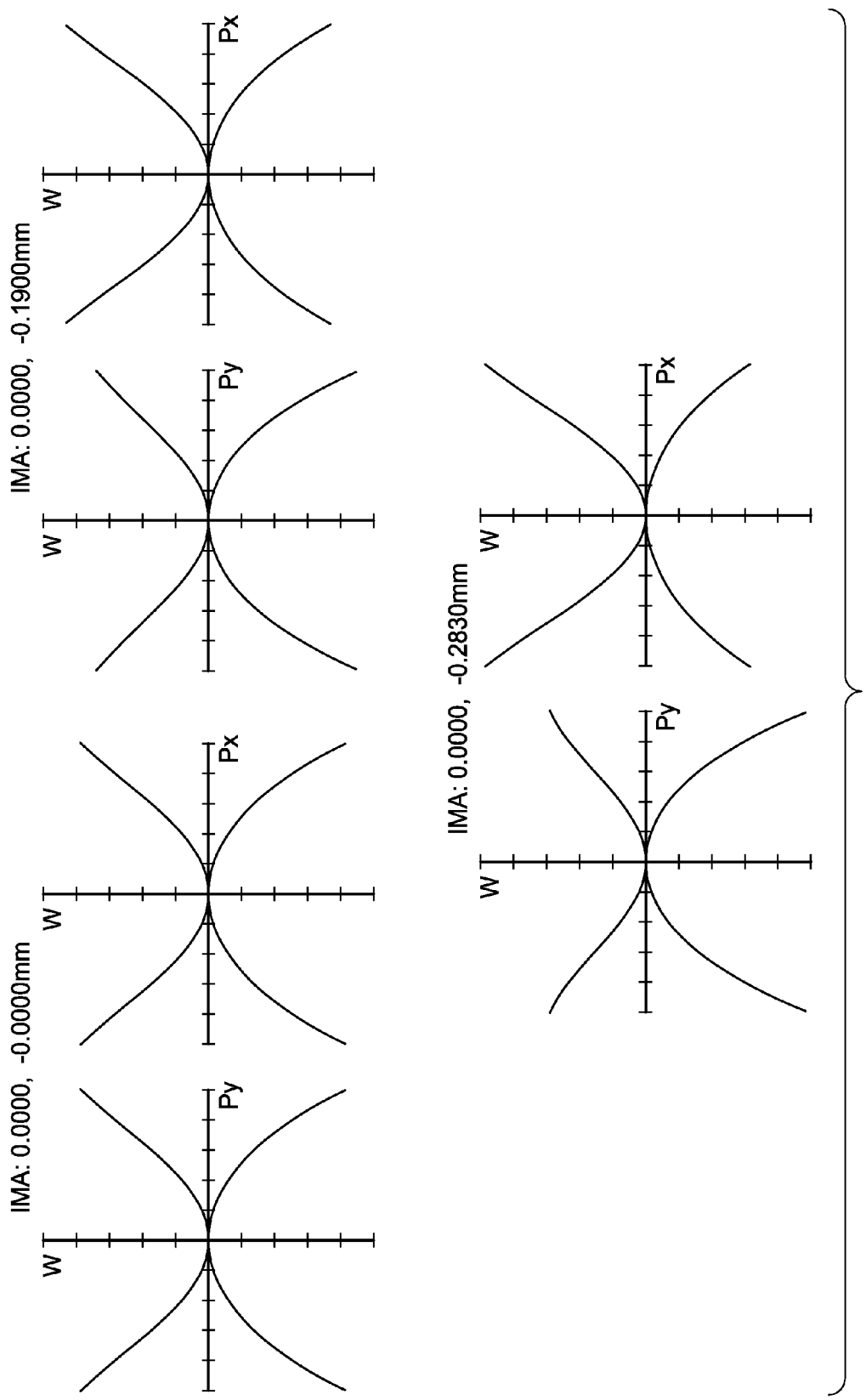

FIGS. 25 and 26 show, with respect to 3D layout of a pupil relay of FIG. 24, relay performance for a 80 nm bandwidth in the form of Optical Path Difference plots, before and after, respectively, changing glass types.

Tables 3 and 4 show Seidel Coefficients; Seidel Aberration Coefficients in Waves (Table 4), along with Lens Data Editor configuration parameters (Table 3).

TABLE 3

Lens Data Editor: Config 2/3

| Surf: | Type | Comment | Radius | | Thickness | | Glass | |
|---|---|---|---|---|---|---|---|---|
| OBJ | Standard | | Infinity | | Infinity | | | |
| STO | Standard | STO | Infinity | | 10.454 | V | | |
| 2* | Standard | BCX1, Thor LB1 ... | 20.100 | | 2.800 | | N-BK7 | |
| 3* | Standard | BCX1, Thor LB ... | −20.100 | | 0.100 | | | |
| 4* | Standard | PCX1, CVI LPX ... | 8.800 | | 2.500 | | N-BK7 | |
| 5* | Standard | PCX1, CVI LPX ... | Infinity | | 0.400 | | | |
| 6* | Standard | PCV1, custom | −33.242 | V | 3.500 | | SFL6 | |
| 7* | Standard | PCV1, custom | Infinity | | 0.186 | V | | |
| 8* | Standard | glass rod | Infinity | | 20.000 | | F2 | |
| 9* | Standard | glass rod | Infinity | | 0.186 | P | | |
| 10* | Standard | PCV2, custom | Infinity | P | 3.500 | P | SFL6 | P |
| 11* | Standard | PCV2, custom | 33.242 | P | 0.400 | P | | |
| 12* | Standard | PCX2, CVI LPX ... | Infinity | P | 2.500 | P | N-BK7 | P |
| 13* | Standard | PCX2, CVI LPX ... | −8.800 | P | 0.100 | P | | |
| 14* | Standard | BCX2, Thor LB ... | 20.100 | P | 2.800 | P | N-BK7 | P |
| 15* | Standard | BCX2, Thor LB ... | −20.100 | P | 10.585 | C | | |
| 16 | Standard | | Infinity | | 4.100 | | | |
| 17* | Paraxial | | | | 4.100 | | | |
| 18 | Standard | | Infinity | | 0.000 | | | |
| 19 | Coordinat ... | | | | 0.000 | | — | |
| IMA | Standard | | −10.045 | V | — | | | |

TABLE 4

Seidel Coefficients
Seidel Aberration Coefficients in Waves:

| Surf | W040 | W131 | W222 | W220P | W311 | W020 | W111 |
|---|---|---|---|---|---|---|---|
| STO | −0.000000 | 0.000000 | −0.000000 | −0.000000 | 0.000000 | −0.000000 | 0.000000 STO |
| 2 | 0.027757 | −0.156106 | 0.219482 | 0.071959 | −0.510933 | −0.163783 | 0.460551 BCX1, Thor LB1212 |
| 3 | 0.353290 | −0.105439 | 0.007867 | 0.071959 | −0.011325 | −0.305591 | −0.045602 BCX1, Thor LB1212 |
| 4 | −0.012911 | 0.073229 | −0.103832 | 0.164360 | −0.318873 | −0.179806 | 0.509901 PCX1, CVI LPX-6.0-8.8-C |
| 5 | 0.515330 | −0.237594 | 0.027386 | −0.000000 | −0.003157 | −0.268716 | −0.061946 PCX1, CVI LPX-6.0-8.8-C |
| 6 | −0.936077 | 0.816735 | −0.178152 | −0.056841 | 0.063657 | 0.941327 | −0.410658 PCV1, custom |
| 7 | 0.264515 | 0.004172 | 0.000016 | 0.000000 | 0.000000 | −0.497297 | −0.003922 PCV1, custom |
| 8 | −0.229437 | −0.003619 | −0.000014 | −0.000000 | −0.000000 | 0.296707 | 0.002340 glass rod |
| 9 | −0.229488 | −0.003620 | −0.000014 | −0.000000 | −0.000000 | 0.296773 | −0.002341 glass rod |
| 10 | 0.264572 | 0.004173 | 0.000016 | 0.000000 | 0.000000 | −0.497404 | −0.003923 PCV2, custom |
| 11 | −0.936363 | −0.846481 | −0.191307 | −0.056841 | −0.068928 | 0.941531 | 0.425576 PCV2, custom |
| 12 | 0.515454 | 0.253905 | 0.031268 | −0.000000 | 0.003850 | −0.268766 | −0.066195 PCX2, CVI LPX-6.0-8.8-C |

TABLE 4-continued

Seidel Coefficients
Seidel Aberration Coefficients in Waves:

| Surf | W040 | W131 | W222 | W220P | W311 | W020 | W111 |
|---|---|---|---|---|---|---|---|
| 13 | −0.012903 | −0.073566 | −0.104856 | 0.164360 | 0.319082 | −0.179889 | −0.512806 PCX2, CVI LPX-6.0-8.8-C |
| 14 | 0.353339 | 0.116599 | 0.009619 | 0.071959 | 0.012666 | −0.305638 | −0.050429 BCX2, Thor LB1212 |
| 15 | 0.027797 | 0.157152 | 0.222120 | 0.071959 | 0.517362 | −0.163854 | −0.463187 BCX2, Thor LB1212 |
| 16 | 0.000000 | 0.000000 | 0.000000 | −0.000000 | −0.000000 | 0.000000 | 0.000000 |
| 17 | 0.000000 | 0.000000 | 0.000000 | 0.000000 | 0.000000 | 0.000000 | 0.000000 |
| 18 | −0.000000 | −0.000000 | −0.000000 | −0.000000 | −0.000000 | −0.000000 | −0.000000 |
| 19 | −0.000000 | −0.000000 | −0.000000 | −0.000000 | −0.000000 | −0.000000 | −0.000000 |
| IMA | 0.000000 | 0.000000 | 0.000000 | 0.000000 | 0.000000 | 0.000000 | 0.000000 |
| TOT | −0.035126 | −0.000459 | −0.060401 | 0.502872 | 0.003402 | −0.354406 | −0.002863 |

VHIS Endoscope Objective Module Design Rules.

General concepts according to further aspects of the invention:
  A microscope objective is required at the distal end of the endoscope for observation of a sample;
  This microscope objective is independently aberration-corrected from the rest of the endoscope so that it can mate to the assembly with loose tolerances;
Design requirements & exceptions:
  The nominal wavefront in the entrance pupil is planar and has a specified angular bandwidth;
  The nominal wavefront in the exit pupil is corrected to be within the diffraction limit or better;
  For a VHIS system, axial chromatic aberration may be excluded from analysis because each field point is monochromatic. Focus shift across the field of view is compensated by slightly tilting the object plane;
  Field curvature may be excluded from analysis because the object plane can be curved a small amount to compensate this aberration; and
  Unit magnification is infinite (infinite-conjugate system).
Design Method; particular preferred aspects:
  Use a commercially-available molded aspheric lens for the objective;
  Correct the off-axis coma in the asphere by breaking symmetry in a designated relay group;
  Designate 2 surfaces in a relay group for the independent correction of spherical aberration and astigmatism;
  Correct field curvature by having positive and negative lenses;
  Extend the physical distance of the unit by introducing a Hopkins rod lens of zero power;
  Use all the same glass type (e.g., N-BK7) for availability of components; and
  All elements are of a simple shape type (piano-convex, plano-concave, bi-convex) for ease of manufacturing.

Figure 27:
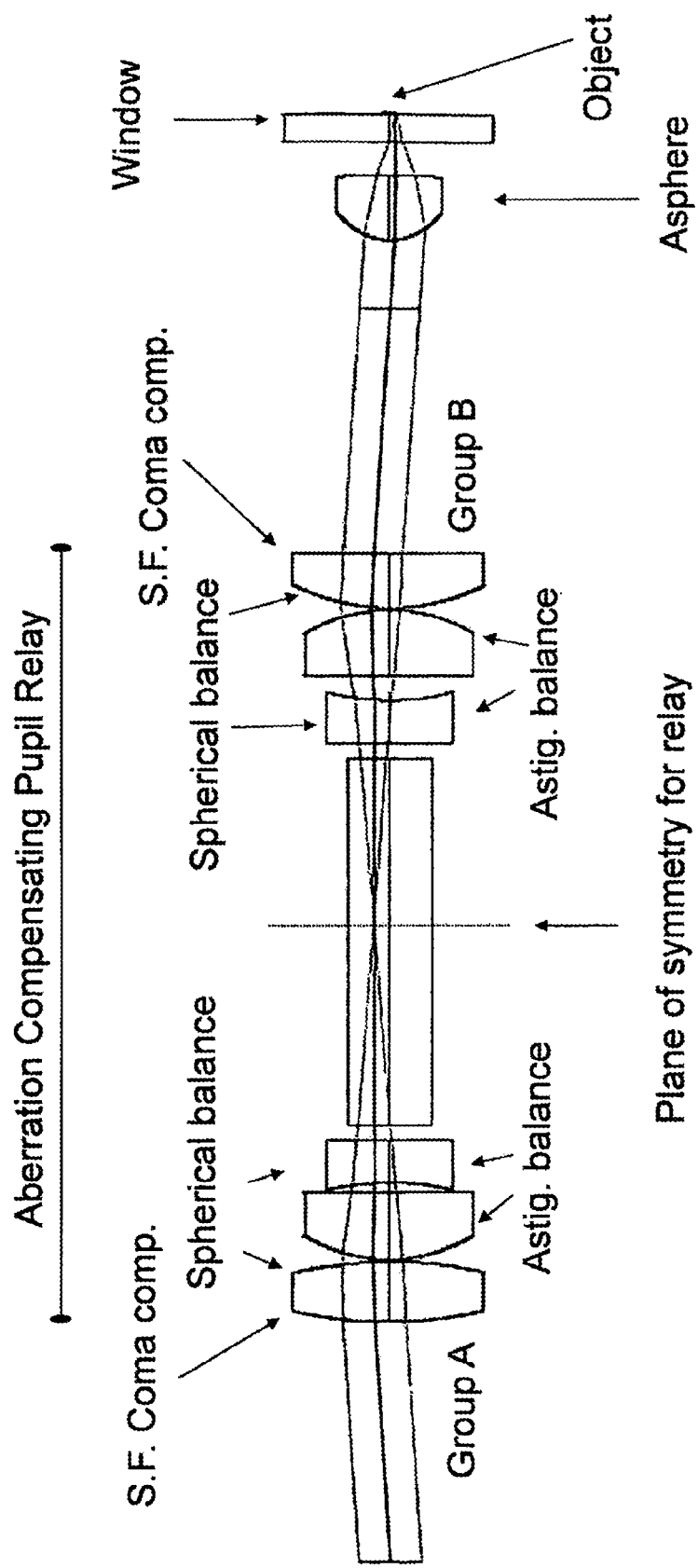
FIG. 27 shows an endoscope microscope objective module according to the present invention. Shown are Group A and Group B elements divided by a plane of symmetry of the relay.

FIG. 27 shows an endoscope microscope objective module according to the present invention. Shown are Group A and Group B elements divided by a plane of symmetry of the relay. According to preferred aspects of the invention: Group A and Group 8 have the same focal length; Coma in the asphere is corrected by changing the shape factors of the 1st element of Group A and the last element of Group B; and Spherical aberration and astigmatism are controlled using the same surfaces as the pupil relays (note: this relay has a non-zero coma and astigmatism result).

Figure 28:
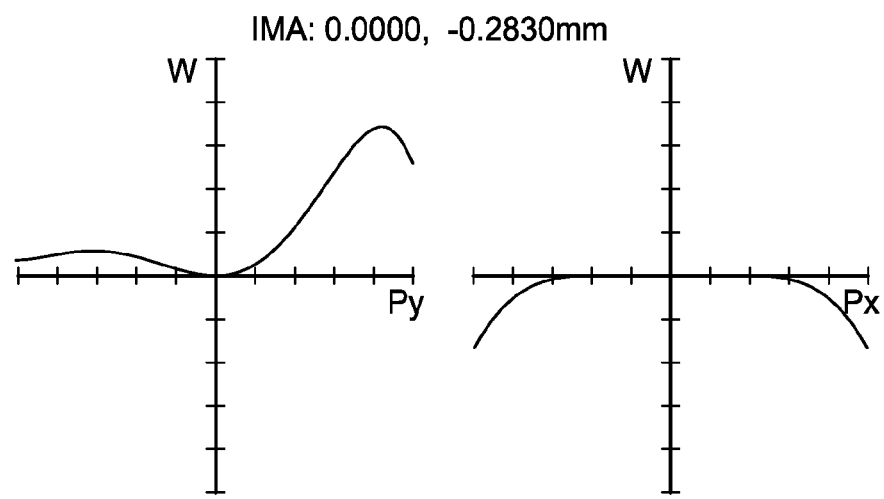
FIG. 28 shows Optical Path Difference plots with respect to the endoscope microscope objective module of FIG. 27, showing OPD correction for the full field angle of ~0.25 waves.

FIG. 28 shows Optical Path Difference plots with respect to the endoscope microscope objective module of FIG. 27, showing OPD correction for the full field angle of ~0.25 waves.

Extending the Objective Design to a Generalized Endoscope Objective Module.

Design improvements according to aspects of the present invention:
  Correction of axial color can be achieved by changing the glass type of the negative element (change to a flint element with Abbe# less than 35). The radius of S6 must be changed to maintain correction of the Ws and Wa totals; and
  Keeping the airspace small (<0.2 mm) between the negative element and the glass rod can keep S7 and S8 from contributing to the wavefront aberration total.

The terms and expressions which have been employed in the foregoing specification are used therein as terms of description and not of limitation, and there is no intention, in the use of such terms and expressions, to exclude equivalents of the features shown and described or portions thereof, it being recognized that the scope of the invention is defined and limited only by the claims that follow.

The invention claimed is:

1. A modular volume holographic imaging system (VHIS) endoscopic system, comprising:
  an endoscope attachment module having
    an observing end and a distal attachment end,
    a microscope objective lens positioned at the observing end,
    a single or cascaded compensated relay system having one or a plurality of pupil relays positioned between the objective lens and the distal attachment end and configured to preserve an optical wavefront for use with a single or multiplexed volume hologram to select wavefronts originating from different object depths, and
    a system aperture with pupil positioned between the objective lens and the one or the plurality of pupil relays; and
  a handle module configured to be reversibly attachable for operative communication with the endoscope attachment module, and having
    a beam splitter,
    a relay having adjustable spacing for object space focus compensation, and a single or multiplexed volume hologram suitable in operation to select wavefronts originating from different object depths, and wherein the handle module is further configured for operative communication with an illumination source and imaging optics.

2. The volume holographic imaging system (VHIS) endoscopic system of claim 1, further comprising an illumination module in operative communication with the handle module, and having a light source, and a source lens 664, and optionally having an illumination hologram, and/or a relay, wherein the source lens is operatively positioned between the light source and the illumination hologram, which is operatively positioned between the source lens and the relay, and wherein the illumination module is optionally configured as a module that is reversibly attachable to the handle module.

3. The volume holographic imaging system (VHIS) endoscopic system of claim 2, wherein the illumination module comprises a Koehler illumination system that provides broadband illumination, and/or a confocal rainbow illumination system configured within the endoscopic system for provide for rejecting out-of-plane scattering sources.

4. The volume holographic imaging system (VHIS) endoscopic system of claim 3, wherein the illumination module comprises a confocal rainbow illumination system configured within the system to disperse monochromatic illumination across the object field, and wherein the dispersed light is matched angularly to the imaging hologram inside the handle module to provide an optical sectioning effect capable of eliminating energy from out-of-plane scattering sources in the object.

5. The volume holographic imaging system (VHIS) endoscopic system of claim 1, further comprising an imaging module, in operative communication with the handle module, and having a collector lens, configured within the imaging module to provide for adjustable spacing for image space compensation, and wherein imaging module is optionally configured as a module that is reversibly attachable to the handle module.

6. The volume holographic imaging system (VHIS) endoscopic system of claim 1, further comprising:

an illumination module configured to be in operative, reversibly attachable communication with the handle module, and having a light source, and a source lens, and optionally having an illumination hologram, and/or a relay, wherein the source lens is operatively positioned between the light source and the illumination hologram, which is operatively positioned between the source lens and the relay; and and imaging module configured to be in operative, reversibly attachable communication with the handle module, and having a collector lens, configured within the imaging module to provide for adjustable spacing for image space compensation.

7. The volume holographic imaging system (VHIS) endoscopic system of claim 1, wherein the endoscope attachment module comprises a plurality of relay stages configured to produce an image of the system aperture at the output (distal attachment end) of the endoscope attachment module.

8. The volume holographic imaging system (VHIS) endoscopic system of claim 1, wherein the endoscope attachment module comprises: a microscope objective; an objective-proximal compensating pupil relay; and a series of modular pupil relays having a combination of bi-convex, planoconvex, and plano-concave lens elements.

9. The volume holographic imaging system (VHIS) endoscopic system of claim 7, wherein a first, objective-proximal, relay stage (compensating pupil relay) is specifically designed and configured to compensate the off-axis aberrations of microscope objective (e.g., an aspheric singlet microscope objective), and wherein a plurality or series of further distal relay stages are corrected for infinite conjugates and configured to be modular.

10. The volume holographic imaging system (VHIS) endoscopic system of claim 9, wherein the plurality or series of further distal modular relay stages (modular pupil relays) are configured to propagate a nominally planar wavefront from the pupil aperture through the system.

11. The volume holographic imaging system (VHIS) endoscopic system of claim 10, wherein the modular pupil relays are corrected for infinite conjugates, and each employ a centrically located Hopkins rod to extend the length of the endoscope attachment module, and wherein the modular pupil relays are configured to be monochromatic at each field angle.

12. The volume holographic imaging system (VHIS) endoscopic system of claim 11, wherein field curvature is removed as an aberration by slightly curving the object plane, and wherein correction of monochromatic aberrations is achieved by using a combination of bi-convex, planoconvex, and plano-concave lens elements.

13. The volume holographic imaging system (VHIS) endoscopic system of claim 12, wherein first and last bi-convex lenses determine spherical aberration of the system, wherein adjusting their radii provides for tuning of the spherical aberration, and wherein inner plano-convex lenses and determine system astigmatism, wherein adjusting their radii provides for tuning of system astigmatism, and wherein negative plano-concave lens elements introduce negative spherical aberration and astigmatism to balance the respective positive elements in the system, and reduce the overall field curvature component of the Seidel sum.

14. The volume holographic imaging system (VHIS) endoscopic system of claim 1, wherein the endoscope attachment module comprises:

an objective module having the microscope objective lens; and a relay module having the single or cascaded compensated relay system having one or a plurality of pupil relays, and wherein the microscope objective is independently aberration-corrected from the rest of the system.

15. The volume holographic imaging system (VHIS) endoscopic system of claim 14, wherein the objective module comprises a diode-collimating asphere as a microscope objective lens, wherein astigmatism is correctable by equally adjusting the radii of the inner plano-convex lens elements of the compensating pupil relay, and wherein coma is correctable by the asymmetry of the first and last lens elements of the compensating pupil relay, and tunable by adjusting the air space between a second plano-concave lens and the subsequent plano-convex lens of the compensating pupil relay.

16. The volume holographic imaging system (VHIS) endoscopic system of claim 1, comprising a common-path broadband light source and source lens to provide illumination at the object plane, wherein the source is positioned so that the source and object planes are confocal, and wherein the hologram disperses light from the source plane such that each point along the dispersive axis of the object plane is essentially monochromatically illuminated, creating an optical sectioning effect with a characteristic optical section thickness.

17. The volume holographic imaging system (VHIS) endoscopic system of claim 1, wherein the endoscope attachment module and the handle module are configured as a flexible endoscopic tip, and additionally comprising, in operative communication with the flexible endoscopic tip, a camera, a flexible cable and a monitor, wherein the flexible cable is suitable to carry both electrical signals from the camera, and further comprising optical fiber suitable for illumination of the tissue sample through the flexible endoscopic tip.

* * * * *